US012435461B2

(12) United States Patent
Kim et al.

(10) Patent No.: US 12,435,461 B2
(45) Date of Patent: Oct. 7, 2025

(54) DRYER AND CONTROL METHOD THEREFOR

(71) Applicant: SAMSUNG ELECTRONICS CO., LTD., Suwon-si (KR)

(72) Inventors: Dokyeong Kim, Suwon-si (KR); Hyejoon Seok, Suwon-si (KR); Minjoon Jung, Suwon-si (KR); Sujin Seong, Suwon-si (KR); Hoon Wee, Suwon-si (KR); Hyungwoo Lee, Suwon-si (KR); Seungeun Chung, Suwon-si (KR); Hankyu Choi, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 767 days.

(21) Appl. No.: 17/851,660

(22) Filed: Jun. 28, 2022

(65) Prior Publication Data

US 2022/0325463 A1 Oct. 13, 2022

Related U.S. Application Data

(63) Continuation of application No. PCT/KR2020/018673, filed on Dec. 18, 2020.

(30) Foreign Application Priority Data

Jan. 2, 2020 (KR) ........................ 10-2020-0000175
Jul. 3, 2020 (KR) ........................ 10-2020-0081955
(Continued)

(51) Int. Cl.
*D06F 58/45* (2020.01)
*A61L 2/04* (2006.01)
(Continued)

(52) U.S. Cl.
CPC ................ *D06F 58/45* (2020.02); *A61L 2/04* (2013.01); *A61L 2/26* (2013.01); *D06F 58/206* (2013.01);
(Continued)

(58) Field of Classification Search
CPC ........ D06F 58/45; D06F 58/40; D06F 58/206; D06F 58/24; A61L 2/04; A61L 2/26; A61L 2202/11
(Continued)

(56) References Cited

U.S. PATENT DOCUMENTS 4,481,786 A * 11/1984 Bashark .............. H02P 23/0077 318/438
4,621,438 A * 11/1986 Lanciaux ................ D06F 58/06 34/604
(Continued)

FOREIGN PATENT DOCUMENTS

DE 102014218254 A1 * 3/2016 ............. D06F 58/50
EP 3191638 B1 * 10/2018 ............. D06F 58/50
(Continued)

OTHER PUBLICATIONS

International Search Report issued in International Application No. PCT/KR2020/018673 dated May 6, 2021.
(Continued)

*Primary Examiner* — Stephen M Gravini
(74) *Attorney, Agent, or Firm* — STAAS & HALSEY LLP

(57) ABSTRACT

A dryer including: a drum; a duct connected to the drum; a compressor connected to an evaporator and a condenser provided inside the duct; a heater provided inside the duct; a fan provided inside the duct; a motor to rotate the fan; and a controller configured to perform a first operation of operating the compressor, the heater, and the motor based on
(Continued)

no object being inside the drum, and a second operation of operating the heater and the motor without operating the compressor. The dryer may sterilize the inside of the dryer, particularly, a flow path through which humid air passes.

20 Claims, 22 Drawing Sheets

(30) Foreign Application Priority Data

Sep. 16, 2020 (KR) ........................ 10-2020-0118919
Dec. 1, 2020 (KR) ........................ 10-2020-0165501

(51) Int. Cl.
*A61L 2/26* (2006.01)
*D06F 58/20* (2006.01)
*D06F 58/24* (2006.01)
*D06F 58/40* (2020.01)

(52) U.S. Cl.
CPC .............. *D06F 58/24* (2013.01); *D06F 58/40* (2020.02); *A61L 2202/11* (2013.01)

(58) Field of Classification Search
USPC ............................................................ 34/602
See application file for complete search history.

(56) References Cited

U.S. PATENT DOCUMENTS

| | | | | |
|---|---|---|---|---|
| 7,020,985 | B2 * | 4/2006 | Casey | D06F 58/206<br>34/595 |
| 8,353,114 | B2 * | 1/2013 | Beers | D06F 58/26<br>68/207 |
| 8,863,400 | B2 * | 10/2014 | Ahn | D06F 58/206<br>34/607 |
| 8,898,927 | B2 * | 12/2014 | Shan | F26B 23/00<br>236/51 |
| 9,091,015 | B2 * | 7/2015 | Caldeira | D06F 58/206 |
| 9,146,056 | B2 * | 9/2015 | Lee | F26B 21/086 |
| 10,465,332 | B2 * | 11/2019 | Simon | D06F 58/50 |
| 11,885,536 | B2 * | 1/2024 | Ko | D06F 58/38 |
| 2005/0066538 | A1 * | 3/2005 | Goldberg | D06F 58/206<br>34/218 |
| 2022/0325463 | A1 * | 10/2022 | Kim | A61L 2/06 |
| 2024/0125039 | A1 * | 4/2024 | Park | D06F 58/206 |

FOREIGN PATENT DOCUMENTS

| | | | | |
|---|---|---|---|---|
| JP | 2007-105238 | A | 4/2007 | |
| JP | 2014-068655 | A | 4/2014 | |
| JP | 5916395 | B2 | 5/2016 | |
| KR | 10-0424071 | B1 | 3/2004 | |
| KR | 10-2009-0127824 | A | 12/2009 | |
| KR | 10-1136861 | B1 | 4/2012 | |
| KR | 10-1337820 | B1 | 12/2013 | |
| KR | 10-2015-0031996 | A | 3/2015 | |
| KR | 10-2017-0084904 | A | 7/2017 | |
| KR | 10-2019-0046599 | A | 5/2019 | |
| KR | 10-1994840 | B1 | 7/2019 | |
| WO | WO-2021137487 | A1 * | 7/2021 | D06F 58/45 |

OTHER PUBLICATIONS

International Written Opinion issued in International Application No. PCT/KR2020/018673 dated May 6, 2021.

* cited by examiner

FIG. 22

| STERILIZATION TIME | 140 MINUTES | 230 MINUTES |
|---|---|---|
| DRUM: INLET | 99.96 | 99.99 |
| FILTER | - | >99.99 |
| FAN | 99.91 | 99.97 |
| REAR DUCT | - | 99.93 |
| HEATER | - | 99.97 |
| FRONT SURFACE OF EVAPORATOR | - | 99.99 |
| BOTTOM OF EVAPORATOR | - | 99.97 |
| BOTTOM OF CONDENSER | - | >99.99 |

DRYER AND CONTROL METHOD THEREFOR

CROSS-REFERENCE TO RELATED APPLICATIONS

This application is a continuation application, under 35 U.S.C. § 111(a), of International Patent Application No. PCT/KR2020/018673, filed on Dec. 18, 2020, which claims the benefit of Korean Patent Application No. 10-2020-0000175, filed Jan. 2, 2020, Korean Patent Application No. 10-2020-0081955, filed Jul. 3, 2020, Korean Patent Application No. 10-2020-0118919, filed Sep. 16, 2020, Korean Patent Application No. 10-2020-0165501, filed Dec. 1, 2020, in the Korean Intellectual Property Office, the entire disclosures of each of which are incorporated herein by reference as a part of this application.

BACKGROUND

Field

The disclosure relates to a dryer and a control method therefor, and more particularly, to a dryer capable of effectively removing condensed water formed on a lower surface of an evaporator and sterilizing the inside, and a control method therefor.

Description of Related Art

In general, a dryer includes a drum rotatably installed therein and dries objects to be dried by passing hot and dry air through the drum while rotating the drum.

A dryer can be provided as an independent apparatus for drying objects to be dried, and a washing machine capable of performing a drying operation can function as a dryer.

Dryers are classified into a circulating type dryer and an exhaust type dryer according to methods of processing air for drying. The exhaust type dryer discharges humid air passed through the drum to the outside of the dryer.

The circulating type dryer circulates humid air passed through the drum inside the dryer without discharging the air to the outside. More specifically, the circulating type dryer dehumidifies humid air passed through the drum and then heats the air such that the dehumidified/heated air dries objects to be dried by passing through the drum.

As such, because humid air circulates inside the circulating type dryer, micro-organisms (for example, mold, germs, etc.) remaining on objects to be dried may move to the inside of the dryer through the humid air and spread inside the dryer. Also, upon condensation of water vapor of humid air, micro-organisms may spread in the remaining condensed water.

SUMMARY

A dryer according to an aspect of the disclosure includes: a drum; a duct connected to the drum; a compressor connected to an evaporator and a condenser provided inside the duct; a heater provided inside the duct; a fan provided inside the duct; a motor to rotate the fan; and a controller configured to perform a first operation of operating the compressor, the heater, and the motor based on no object being inside the drum, and a second operation of operating the heater and the motor without operating the compressor.

A method for controlling a dryer, according to an aspect of the disclosure, the dryer including a drum, a duct connected to the drum, a compressor connected to an evaporator and a condenser provided inside the duct, a heater provided inside the duct, a fan provided inside the duct, and a motor to rotate the fan, includes: a first operation of operating the compressor, the heater, and the motor based on no object being inside the drum; and a second operation of operating the heater and the motor without operating the compressor.

A dryer according to an aspect of the disclosure includes: a drum; a duct connected to the drum; a compressor connected to an evaporator and a condenser provided inside the duct; a heater provided inside the duct; a fan provided inside the duct; a motor rotate the fan; and a controller configured to operate the compressor, the heater, and the motor based on no object being inside the drum.

BRIEF DESCRIPTION OF THE DRAWINGS

FIG. 22 shows a sterilization effect by a sterilization operation according to an embodiment.

DETAILED DESCRIPTION

Figure 1:
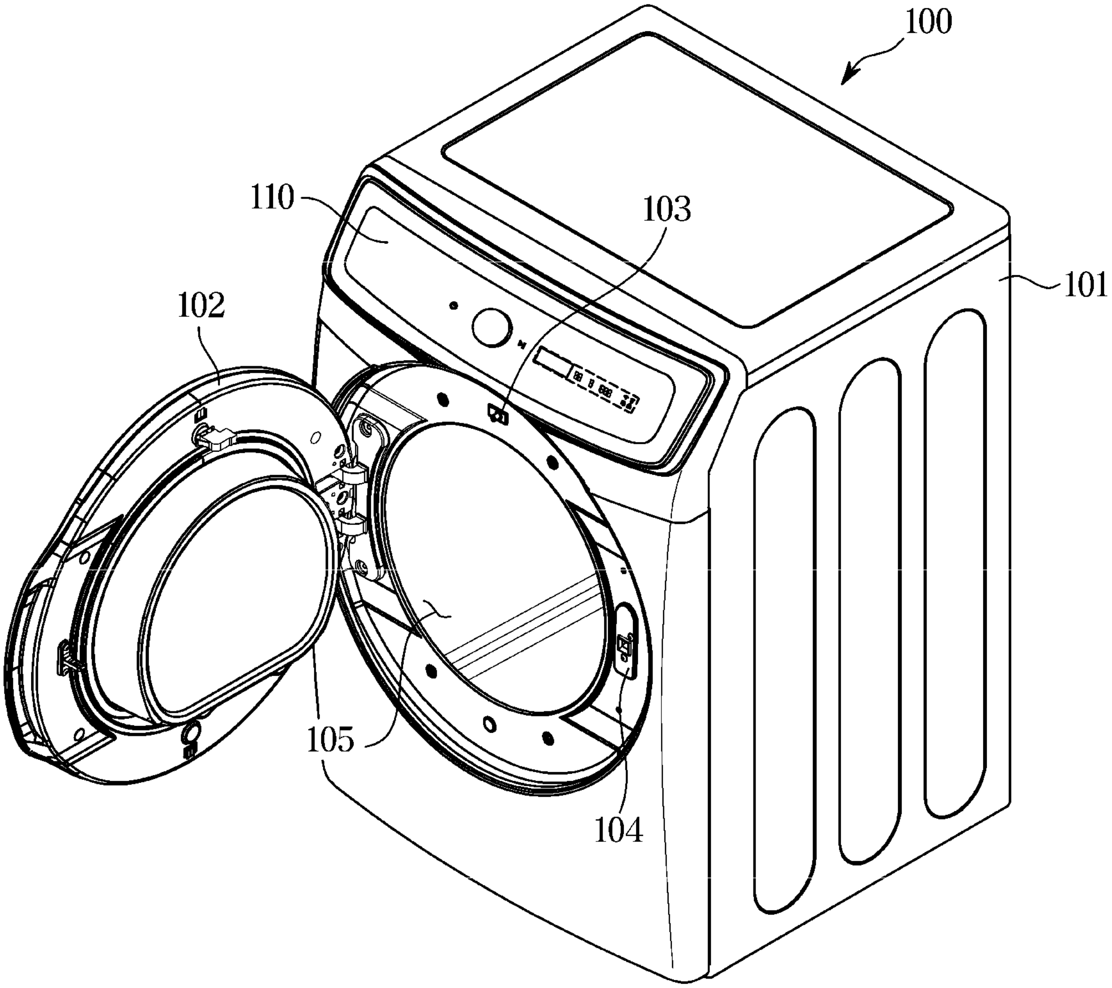
FIG. 1 shows a dryer according to an embodiment.

Like reference numerals will refer to like components throughout this specification. This specification does not describe all components of the embodiments, and general information in the technical field to which the present disclosure belongs or overlapping information between the embodiments will not be described. As used herein, the terms "portion", "part, "module, "member" or "block" may be implemented as software or hardware, and according to embodiments, a plurality of "portions", "parts, "modules, "members" or "blocks" may be implemented as a single component, or a single "portion", "part, "module, "member" or "block" may include a plurality of components.

In the entire specification, it will be understood that when a certain part is referred to as being "connected" to another part, it can be directly or indirectly connected to the other part. When a part is indirectly connected to another part, it may be connected to the other part through a wireless communication network.

Also, it will be understood that when a certain part "includes" a certain component, the part does not exclude another component but can further include another component, unless the context clearly dictates otherwise.

In the entire specification, it will also be understood that when an element is referred to as being "on" or "over" another element, it can be directly on the other element or intervening elements may also be present.

It will be understood that the terms first, second, etc., may be used only to distinguish one component from another, and these components should not be limited by these terms.

It is to be understood that the singular forms "a," "an," and "the" include plural referents unless the context clearly dictates otherwise.

Reference numerals used in operations are provided for convenience of description, without describing the order of the operations, and the operations can be executed in a different order from the stated order unless a specific order is definitely specified in the context.

An aspect of the disclosure provides a dryer capable of effectively removing condensed water formed on an evaporator after a drying operation is completed, and a control method therefor.

An aspect of the disclosure provides a dryer capable of sterilizing the inside of the dryer, specifically, a flow path through which humid air passes, and a control method therefor.

In the dryer and the control method therefor, according to an aspect of the disclosure, by effectively removing moisture remaining on an evaporator after a drying operation is completed, it may be possible to prevent micro-organisms from spreading inside the dryer and accordingly prevent an unpleasant smell from being generated due to the spread of micro-organisms.

Also, in the dryer and the control method therefor, according to an aspect of the present disclosure, by inducing a user to select an operation of removing moisture remaining on an evaporator, it may be possible to remove moisture remaining on the evaporator in time.

According to an aspect of the disclosure, there may be provided a dryer capable of sterilizing the inside of the dryer, particularly, a flow path through which humid air passes, and a control method therefor. More specifically, the dryer may sterilize micro-organisms spreading in a condenser, an evaporator, a duct, a fan, drum air holes, etc., which are in contact with humid air. Accordingly, it may be possible to prevent or reduce a bad smell, contamination, etc., which are caused by micro-organisms, while preventing or reducing micro-organisms spreading in the dryer from being transferred to objects to be dried.

Hereinafter, an operation principle and embodiments of the present disclosure will be described with reference to the accompanying drawings.

Figure 2:
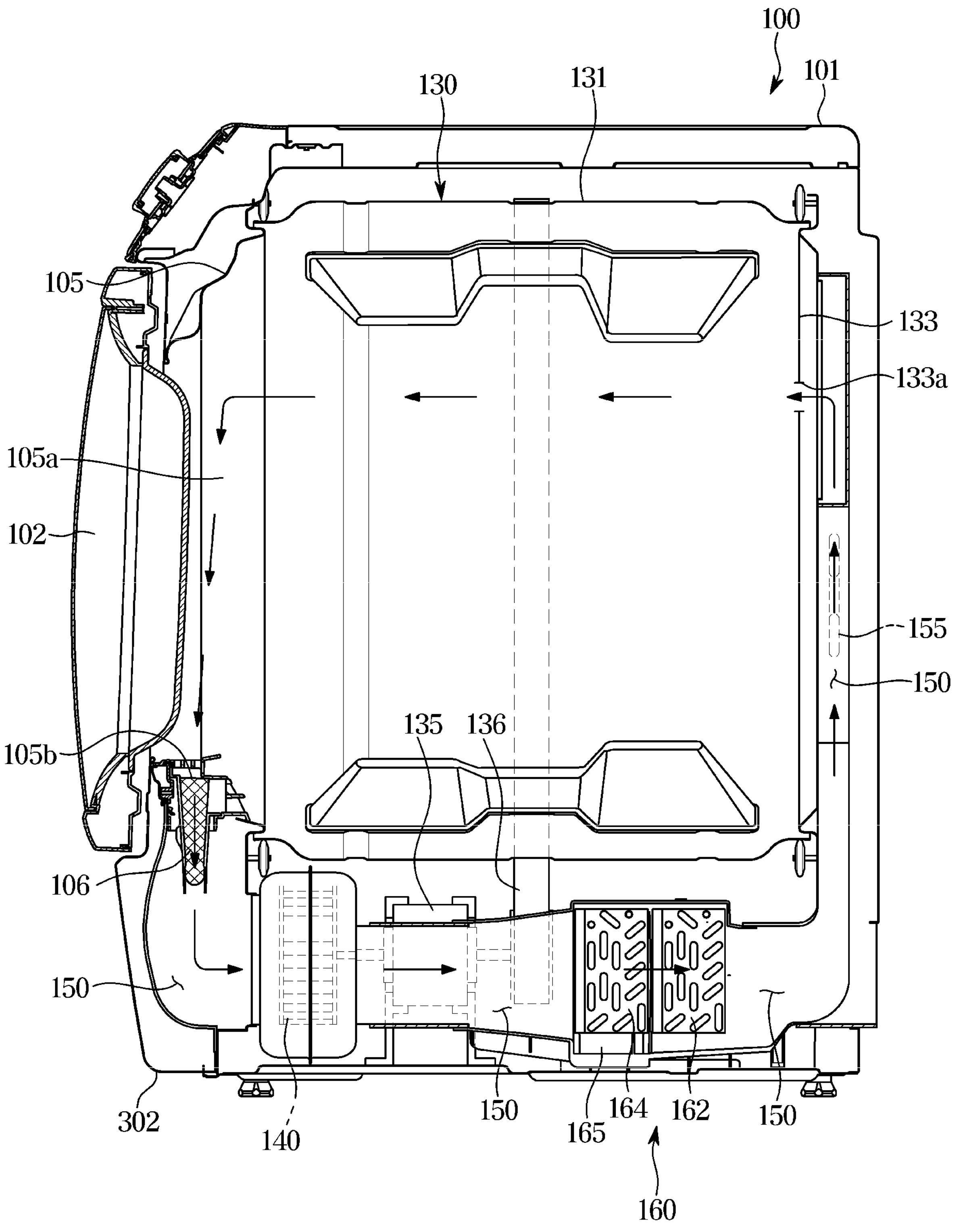
FIG. 2 shows a side cross section of a dryer according to an embodiment.
Figure 3:
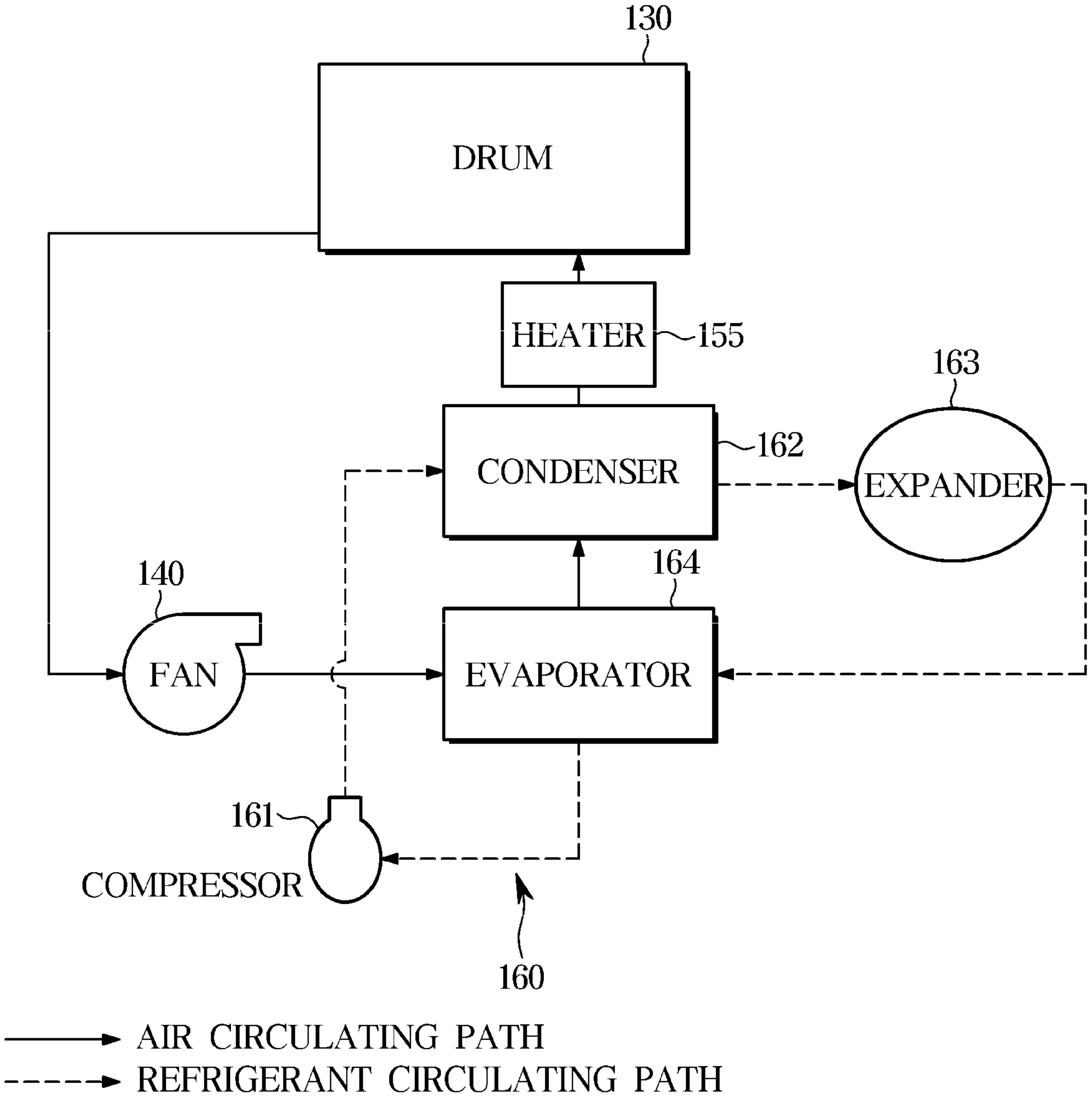
FIG. 3 shows air circulation and refrigerant circulation of a dryer according to an embodiment.

FIG. 1 shows a dryer according to an embodiment. FIG. 2 shows a side cross section of a dryer according to an embodiment. FIG. 3 shows air circulation and refrigerant circulation of a dryer according to an embodiment.

A configuration of a dryer 100 will be described with reference to FIGS. 1, 2, and 3.

The dryer 100 may include a cabinet 101. The cabinet 101 may be substantially in a shape of a rectangular parallelepiped box. Also, the dryer 100 may include a door 102, a control panel 110, a drum 130, a drum motor 135, a fan 140, a duct 150, a heater 155, and a heat pump 160, which are accommodated in the cabinet 101.

In a front center of the cabinet 101, an entrance 101*a* for putting-in or taking-out of an object to be dried may be provided.

The door 102 may open or close the entrance 101*a*, and closing of the entrance 101*a* by the door 102 may be sensed by a door switch 103. According to closing of the entrance 101*a* and operation of the dryer 100, the door 102 may be locked by a door lock 104.

In a front upper portion of the cabinet 101, the control panel 110 including a user inputter for obtaining a user input with respect to the dryer 100 from the user and a display for displaying operation information of the dryer 100 may be provided. The control panel 110 will be described in more detail, below.

The dryer 100 may include the drum 130 for accommodating an object to be dried and drying the object to be dried. The drum 130 may be rotatably installed inside the cabinet 101. The object to be dried may include all objects that can be dried by hot air. For example, the object to be dried may include products made of fiber, such as clothes, towels, shoes, etc., leather, etc.

The drum 130 may include a drum body 131 formed in a shape of a cylinder of which the center of rotation is in a front-back horizontal direction. At least one lifter may protrude from an inner wall of the drum body 131 to support tumbling of laundry.

A rear side of the drum body 121 may be closed by a rear panel 133 including an inlet 133*a* through which hot and dry air enters.

The drum 130 may rotate by receiving a rotation force from the drum motor 135. The drum 130 may be connected to the drum motor 135 installed in the cabinet 101 by a belt 136. The drum motor 135 may provide a rotation force to the drum 130 through the belt 136.

In front of the drum 130, a front frame 105 for rotatably fixing the drum 130 may be provided. In a center portion of the front frame 105, an opening 105*a* for putting-in or taking-out of an object to be dried may be formed.

Also, in the front frame 105, an outlet 105*a* through which air passed through the drum 130 is discharged may be provided. In the outlet 105*b*, a filter 106 for collecting foreign materials generated from the object to be dried may be installed. Accordingly, foreign materials generated from the object to be dried may be collected by the filter 106.

Air entered the drum 130 through the inlet 133*a* may be used to dry an object to be dried, and then discharged to the duct 150 from the drum 130 through the outlet 105*b*. The air used to dry the object to be dried and then discharged to the duct 150 may change to hot and dry air by passing through the heat pump 160, and then again enter the drum 130 through the inlet 133*a*.

In the dryer 100, at least one heat source may be provided, and the dryer 100 may supply hot air to the drum 130 through the heat source. For example, the dryer 100 may include the heater 155 and the heat pump 160 as the heat source.

In this case, dryers including heat pumps constituting refrigerant circuits may be classified into a circulating type dryer and an exhaust type dryer according to the flow of circulating air. The circulating type dryer is a dryer capable of drying objects through circulation without discharging or sucking air. The exhaust type dryer is a dryer that sucks outside air, uses the air for drying, and then discharges the air to the outside of the dryer.

The dryer 100 may include the fan 140 for circulating inside air of the drum 130. The fan 140 may suck air from inside of the drum 130, and discharge the air to the duct 150. Inside air of the drum 130 may be circulated through the drum 130 and the duct 150 by the fan 140.

The fan 140 may rotate by the drum motor 135. In other words, the drum motor 135 may provide a rotation to both the drum 130 and the fan 140. For example, as shown in FIG. 2, the drum motor 135 may provide a rotation to the fan 140 through a rotation shaft, and also provide a rotation to the drum 130 through a pulley and a belt, although not limited thereto. However, the fan 140 may rotate by a fan motor provided separately from the drum motor 135.

On the duct 150 through which inside air of the drum 130 circulates, the heater 155 and the heat pump 160 may be provided.

The heat pump 160 may include a compressor 161, a condenser 162, an evaporator 164, and an expander 163, as shown in FIG. 3. The compressor 161, the condenser 162, the evaporator 164, and the expander 163 may be rested on a lower surface of the cabinet 101.

The compressor 161 may compress a refrigerant in a gaseous state to a high-temperature and high-pressure state, and discharge a high-temperature and high-pressure gaseous refrigerant. For example, the compressor 161 may compress the refrigerant through a reciprocating motion of a piston or a rotational motion of a rotor. The discharged refrigerant may be transferred to the condenser 162.

The condenser 162 may condense the compressed gaseous refrigerant to a liquid. The condenser 162 may release heat to the surroundings through a condensation process of the refrigerant. The condenser 162 may be provided on the duct 150, and heat air through heat generated in the condensation process of the refrigerant. The liquid refrigerant condensed in the condenser 162 may be transferred to the expander 163.

The expander 163 may expand the high-temperature and high-pressure liquid refrigerant condensed in the condenser 162 to a liquid refrigerant in a low-pressure state. For example, the expander 163 may include an electronic expansion valve for adjusting pressure of a liquid refrigerant, wherein an open value of the electronic expansion valve may vary by a capillary tube and an electrical signal.

The evaporator 164 may evaporate the liquid refrigerant expanded by the expander 163. As a result, the evaporator 164 may return a low-temperature and low-pressure gaseous refrigerant to the compressor 161.

The evaporator 164 may absorb heat from the surroundings through an evaporation process of changing a low-pressure liquid refrigerant to a gaseous refrigerant. The evaporator 164 may be provided on the duct 150, and cool air passing through the evaporator 164 during the evaporation process.

Surrounding air may be cooled by the evaporator 164, and, when temperature of the surrounding air falls below a dew point, the surrounding air of the evaporator 164 may be condensed. Water condensed on the evaporator 164 may fall by gravity and be accommodated in a water bucket 165 provided below the evaporator 164. At this time, a part of the water condensed on the evaporator 164 may remain on the evaporator 164 by surface tension.

Water collected in the water bucket 165 may move to a separate storage, or may be drained to the outside of the dryer 100. For example, water collected by the water bucket 165 may flow along a drain hose and be drained to the outside of the dryer 100 according to an operation of a drain pump. Also, water collected by the water bucket 165 and moved to the separate storage may flow along the drain hose and be drained to the outside of the dryer 100 according to an operation of the drain pump.

As such, due to condensation around the evaporator 164, absolute humidity of air passing through the evaporator 164 may be lowered. In other words, an amount of water vapor included in air passing through the evaporator 164 may be reduced. By using such condensation around the evaporator 164, the dryer 100 may reduce an amount of water vapor included in inside air of the drum 130, and also dry an object to be dried.

Inside air of the drum 130 may be sucked into the duct 150 by the fan 140. The fan 140, the evaporator 164, the condenser 162, and the heater 155 may be provided inside the duct 150.

The evaporator 164 may be disposed upstream of the condenser 162 with respect to a flow of air by the fan 140. Air sucked from the drum 130 may pass through the evaporator 164 to thereby be dried by the evaporator 164 (water vapor is condensed).

The air passed through the evaporator 164 may move toward the condenser 162. As described above, while a refrigerant is condensed, the condenser 162 may release heat. Thereby, the air passed through the evaporator 164 may be heated by the condenser 162, while passing through the condenser 162.

The air passed through the condenser 162 may move toward the heater 155. The heater 155 may support the condenser 162 to heat air. For example, before the condenser 162 of the heat pump 160 sufficiently heats air of the duct 150, the heater 155 may support the condenser 162 to heat air of the duct 150.

By the heater 155 supporting the condenser 162, inside temperature of the drum 130 may rise more rapidly, and the dryer 100 may dry an object to be dried more rapidly.

The heater 155 may be disposed downstream of the condenser 162 with respect to the flow of air by the fan 140. The heater 155 may be implemented through a heating coil, although not limited thereto. However, the heater 155 may be implemented through various known devices.

Air may be heated by passing through the condenser 162 and the heater 155, and accordingly, relative humidity of the air may be lowered. In other words, air heated by the condenser 162 and the heater 155 may accommodate a larger amount of water vapor.

As such, the air heated by the condenser 162 and the heater 155 may enter the inside of the drum 130 through the inlet 133*a* formed in the rear panel 133 of the drum 130, and absorb moisture from an object to be dried inside the drum 130. The air that has absorbed moisture may move to the evaporator 164 by the fan 140.

As such, air may circulate between the drum 130 and the duct 150, and during circulation of the air, the air may be repeatedly subject to cooling/dehumidification, heating, and moisture absorption.

Figure 4:
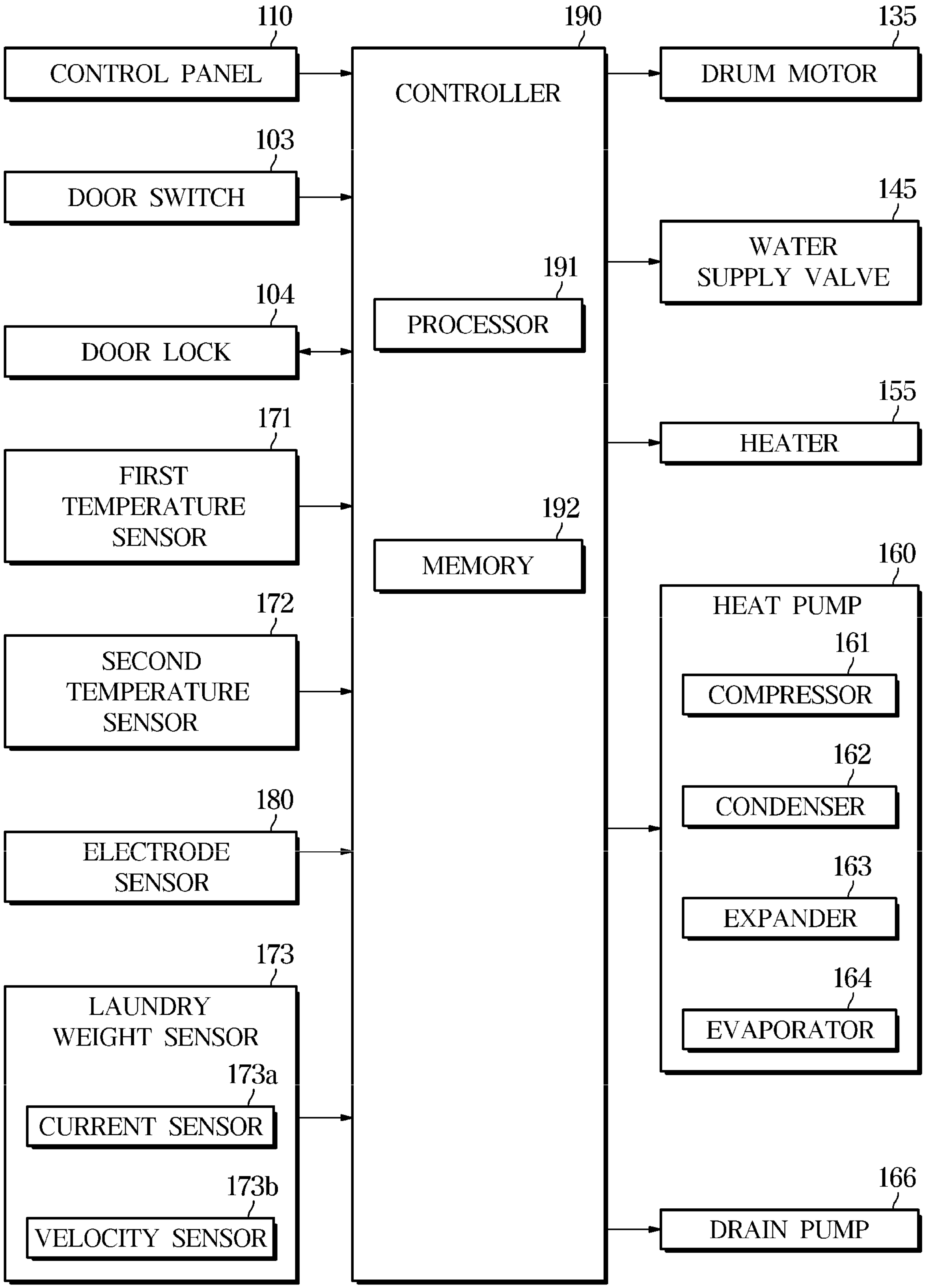
FIG. 4 shows a configuration of a dryer according to an embodiment.
Figure 5:
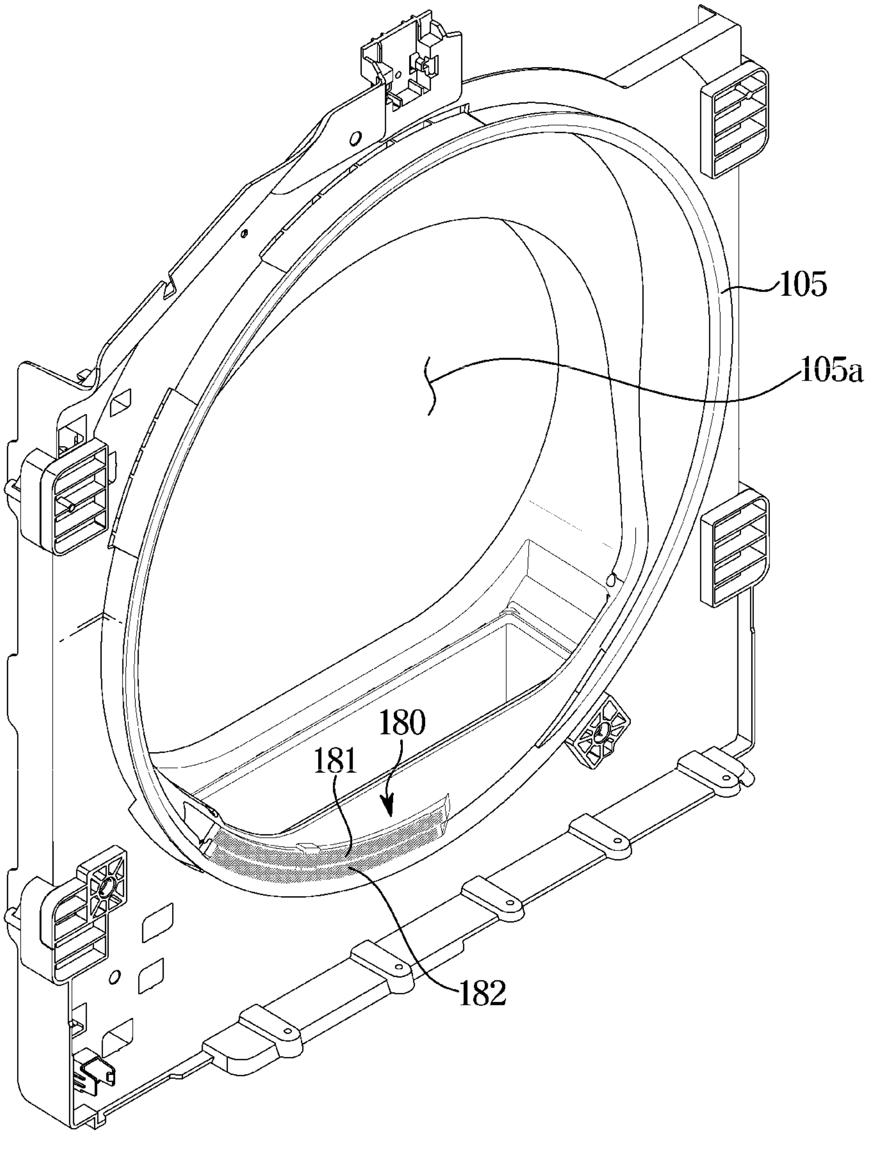
FIG. 5 shows an electrode sensor included in a dryer according to an embodiment.
Figure 6:
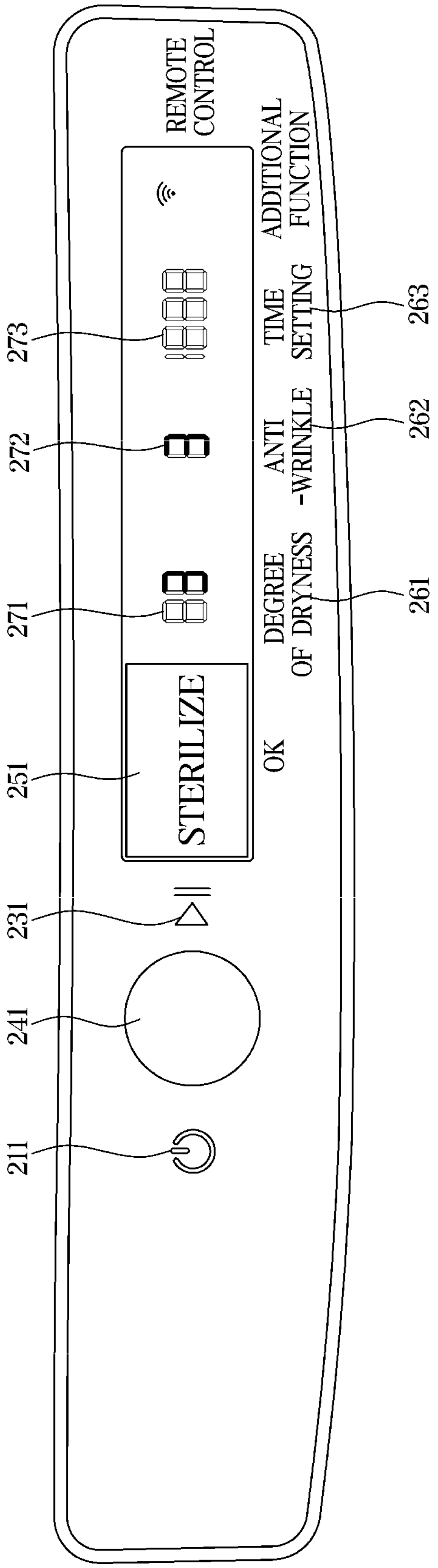
FIG. 6 shows a control panel included in a dryer according to an embodiment.

FIG. 4 shows a configuration of a dryer according to an embodiment. FIG. 5 shows an electrode sensor included in a dryer according to an embodiment. FIG. 6 shows a control panel included in a dryer according to an embodiment.

The dryer 100 may further include the following electrical configurations, in addition to mechanical configurations described together with FIGS. 1, 2, and 3. The dryer 100 may include the drum motor 135, the heater 155, the compressor 161, a drain pump 166, the door switch 103, the door lock 104, the control panel 110, a first temperature sensor 171, a second temperature sensor 172, a laundry weight sensor 173, an electrode sensor 180, and a controller 190.

The drum motor 135 may rotate the drum 130 and the fan 140 in response to a driving signal from the controller 190. The heater 155 may heat air of the duct 150 in response to a heating signal from the controller 190. The compressor 161 may circulate a refrigerant of the heat pump 160 in response to a driving signal from the controller 190.

The door switch 103 may detect a closed state of the door 102 and an open state of the door 102. The door lock 104 may lock the door 102 in response to a lock signal from the controller 190. According to closing of the entrance 101*a* by the door 102 and an operation of the dryer 100, the controller 190 may control the door lock 104 to lock the door 102.

The first temperature sensor 171 may measure temperature of air of the drum 130. For example, the first temperature sensor 171 may be installed at the outlet 105*b* of the front frame 105, and measure temperature of air discharged from the drum 130 to the duct 150.

Because air circulates through the drum 130 and the duct 150 by the fan 140, temperature of air, measured at the outlet 105*b* of the drum 130, may be substantially equal to temperature of inside air of the drum 130.

The first temperature sensor 171 may provide an electrical signal (for example, a voltage signal or a current signal) corresponding to the temperature of the air (air discharged from the drum) of the drum 130 to the controller 190. For example, the first temperature sensor 171 may include a thermistor of which an electrical resistance value changes according to temperature. The thermistor may be connected in series to a reference resistor between a supply voltage and a ground, and the controller 190 may obtain a voltage of a connection node at which the thermistor is connected to the reference resistor.

The controller 190 may identify the temperature of the air of the drum 130 based on the voltage of the connection node. For example, the controller 190 may identify whether the temperature of the air of the drum 130 is higher than first temperature corresponding to a first reference voltage, based on a comparison between the voltage of the connection node and the first reference voltage, and the controller 190 may identify whether the temperature of the air of the drum 130 is higher than second temperature corresponding to a second reference voltage, based on a comparison between the voltage of the connection node and the second reference voltage.

The second temperature sensor 172 may measure temperature of a refrigerant of the compressor 161. For example, the second temperature sensor 172 may be installed at an outlet of the compressor 161, and measure temperature of air discharged from the compressor 161 to the condenser 162.

Because the refrigerant circulates through the refrigerant circuits 161, 162, 163, and 164 by the compressor 161, the temperature of the refrigerant, measured at the outlet of the compressor 161, may be substantially equal to temperature of the refrigerant inside the compressor 161.

The second temperature sensor 172 may provide an electrical signal corresponding to the temperature of the refrigerant (more specifically, a refrigerant discharged from the compressor) of the compressor 161 to the controller 190. For example, the second temperature sensor 172 may include a thermistor. The thermistor may be connected in series to a reference resistor between the supply voltage and the ground, and the controller 190 may obtain a voltage of a connection node at which the thermistor is connected to the reference resistor.

The controller 190 may identify the temperature of the refrigerant of the compressor 161 based on the voltage of the connection node. For example, the controller 190 may identify whether the temperature of the refrigerant of the compressor 161 is higher than the first temperature corresponding to the first reference voltage, based on a comparison between the voltage of the connection node and the first reference voltage, and the controller 190 may identify whether the temperature of the refrigerant of the compressor 161 is higher than the second temperature corresponding to the second reference voltage, based on a comparison between the voltage of the connection node and the second reference voltage.

The laundry weight sensor 173 may be all sensors for sensing an amount of an object to be dried, accommodated in the drum 130.

For example, the laundry weight sensor 173 may include at least one of a current sensor 173*a* for sensing a current value applied to the drum motor 135 for rotating the drum 130, or a velocity sensor 173*b* for sensing a change in velocity of the drum 130.

Upon an object to be dried is inside the drum 130, a current value that is applied to the drum motor 135 may increase, and accordingly, a weight of the object to be dried may be proportional to a current value measured by the current sensor 173*a*. Accordingly, based on an output value of the current sensor 173*a*, which is lower than or equal to a preset value, the controller 190 may determine that no object to be dried is inside the drum 130.

Also, upon an object to be dried is inside the drum 130, a change amount in velocity of the drum 130 may decrease, and accordingly, a weight of the object to be dried may be inversely proportional to a change amount of velocity measured by the velocity sensor 173*b*. Accordingly, based on a change amount of an output value of the velocity sensor 173*b*, which is greater than or equal to a preset value, the controller 190 may determine that no object to be dried is inside the drum 130.

The laundry weight sensor 173 has been described above to include the current sensor 173*a* and/or the velocity sensor 173*b*, however, the laundry weight sensor 173 may be any kind of sensor capable of sensing an amount of an object to be dried inside the drum 130.

The electrode sensor 180 may include a first electrode 181 and a second electrode 182 that is spaced from the first electrode 181.

The electrode sensor 180 may be in contact with an object to be dried to measure an electrical resistance value of the object to be dried or electrical conductivity of the object to be dried. Generally, it is known that electrical conductivity of wet cloth is greater than electrical conductivity of dry cloth. In other words, an electrical resistance value of an object not dried may be smaller than an electrical resistance value of an object dried. Accordingly, a degree of dryness of an object to be dried may be identified based on an electrical resistance value (or electrical conductivity) of the object to be dried.

Also, the electrode sensor 180 may measure a change of capacitance by an object to be dried. For example, capacitance may be generated between the first electrode 181 and the second electrode 182, and the capacitance may change according to a material between the first electrode 181 and the second electrode 182. For example, capacitance of when only air is between the first electrode 181 and the second electrode 182 may be different from capacitance of when an object to be dried is between the first electrode 181 and the second electrode 182. Accordingly, a degree of dryness of an object to be dried may be identified based on capacitance between the first electrode 181 and the second capacitance 182.

The electrode sensor 180 may be provided in a space accommodating an object to be dried in order to be in contact with the object to be dried, or the electrode sensor 180 may be provided in a structure forming the space.

For example, the electrode sensor 180 may be, as shown in FIG. 5, installed on an inner wall of the front frame 105. As described above, the front frame 105 may rotatably support the drum 130 in front of the drum 130. A part (boundary line) at which the front frame 105 is in contact with the cylindrical drum 130 may be substantially in a form of a circle, and the electrode sensor 180 may be located at an inner lower portion of the circular boundary line at which the front frame 105 is in contact with the drum 130.

The first electrode 181 and the second electrode 182, included in the electrode sensor 180, may be arranged in parallel to each other, and may each be in a shape of a circular arc. For example, the first electrode 181 and the second electrode 182 may be in a shape of circular arcs having different diameters.

Due to the arrangement and shape of the electrode sensor 180, the electrode sensor 180 may be in contact with an object to be dried.

However, the shape and arrangement of the electrode sensor 180 are not limited to those shown in FIG. 5. For example, the electrode sensor 180 may be provided on the inner wall of the drum body 131 or on an inner wall of the rear panel 133 in order to be in contact with an object to be dried.

As such, the electrode sensor 180 may be in contact with an object to be dried, and provide an electrical signal (for example, a voltage signal or a current signal) for identifying a degree of dryness of the object to be dried to the controller 190.

For example, the electrode sensor 180 may be connected in series to a reference resistor between the supply voltage and the ground, and the controller 190 may obtain a voltage of a connection node at which the electrode sensor 180 is connected to the reference resistance.

The controller 190 may identify an electrical resistance value (or electrical conductivity) of the object to be dried based on the voltage of the connection node, and may also identify a degree of dryness of the object to be dried based on the voltage of the connection node. For example, the controller 190 may identify whether the object to be dried has been completely dried, based on a comparison between the voltage of the connection node and the first reference voltage.

In addition, the controller 190 may identify whether an object to be dried has been accommodated in the drum 130, based on the voltage of the connection node. Upon putting of an object to be dried into the drum 130, the object to be dried may be in contact with the electrode sensor 180 to change an electrical resistance value and electrical conductivity between the electrode sensor 180, and accordingly, a voltage value of the connection node may change. Based on the voltage value of the connection node, which deviates from a predefined range indicating that no object to be dried is accommodated in the drum 130, the controller 90 may identity that an object to be dried has been accommodated in the drum 130.

As another example, the controller 190 may output a sensing signal for measuring capacitance to the first electrode 181 of the electrode sensor 180, and obtain a response signal corresponding to capacitance from the second electrode 182. The controller 190 may identify capacitance between the first electrode 181 and the second electrode 182 based on a phase difference, etc. between the sensing signal and the response signal, and identify whether an object to be dried has been accommodated in the drum 130 based on the capacitance between the first electrode 181 and the second electrode 182.

The control panel 110 may include the user inputter for obtaining a user input and the display for displaying a drying setting and/or drying operation information in response to a user input. In other words, the control panel 110 may provide an interface (hereinafter, referred to as a 'user interface') for enabling a user to interact with the dryer 100.

The control panel 110 may include, as shown in FIG. 6, a dryer power button 211 for obtaining a user input for powering on the dryer 100 or a user input for powering off the dryer 100. The dryer power button 211 may include a tact switch, a push switch, a slide switch, a toggle switch, a micro switch, or a touch switch. The dryer power button 211 may include, for example, a touch switch. Also, the dryer power button 211 may include a light emitting diode for displaying a power state of the dryer 100.

The control panel 110 may include, as shown in FIG. 6, an operation button 231 for obtaining a user input for starting or pausing a drying operation of the dryer 100. The operation button 231 may include a push switch, a slide switch, a toggle switch, a micro switch, or a touch switch. Also, the operation button 231 may include a light emitting diode for displaying whether or not the dryer 100 operates.

The control panel 110 may further include, as shown in FIG. 6, a dial 241 for obtaining a user input made by a rotation, and a display panel 251 for displaying a drying course selected by a rotation of the dial 241.

The dial 241 may obtain a user input for selecting any one of a drying course, a dehumidification course, or a sterilization course. The display panel 251 may display the drying course, the dehumidification course, or the sterilization course selected by a rotation of the dial 241.

Herein, the drying course may include drying settings (for example, a degree of dryness, an additional time for anti-wrinkle, a drying time, etc.) set in advance by a designer of the dryer 100 according to kinds (for example, bedclothes, underwear, etc.) and materials (for example, wool, etc.) of objects to be dried. For example, standard drying may include drying settings that can be applied to most of drying materials, and bedclothes drying may include drying settings optimized to dry bedclothes.

The dehumidification course may represent an operation of the dryer 100 for removing moisture from parts of the dryer 100, such as the drum 130, the duct 150, the outlet **105*b*, the fan 140, the evaporator 164, the condenser 162, the heater 155, and the inlet 133*a***, through which air flows.

The dehumidification course may represent an operation of dehumidifying the inside of the dryer 100 and is not limited by the term. Also, the dehumidification course may be referred to as various terms. For example, the dehumidification course may be referred to as various terms, such as a dehumidification cycle, a dehumidification operation, a dehumidification algorithm, etc.

The sterilization course may represent an operation of the dryer 100 for washing and sterilizing the parts of the dryer 100, such as the drum 130, the duct 150, the outlet 105*b*, the fan 140, the evaporator 164, the condenser 162, the heater 155, and the inlet 133*a*, through which air flows.

The sterilization course may represent an operation of washing and sterilizing the inside of the dryer 100 and is not limited by the term. Also, the sterilization course may be referred to as various terms. For example, the sterilization course may be referred to as various terms, such as a sterilization cycle, a sterilization operation, a sterilization algorithm, a washing course, a washing cycle, a washing operation, a washing algorithm, self cleaning, self sterilization, steam sterilization, high-temperature sterilization, etc.

The dial 241 may obtain a user input (a dial rotation and stop) for selecting any one course from among a plurality of drying courses and at least one sterilization course. Also, the display panel 251 may display the plurality of drying courses and the at least one sterilization course in a preset order depending on a rotation of the dial 241. A course displayed on the display panel 251 at a time at which the dial 241 stops rotating may be selected.

The display panel 251 may display operation information of the dryer 100 operating. For example, the display panel 251 may display a time left until a drying operation of the dryer 100 is completed.

The display panel 251 may include, for example, a liquid crystal display (LCD) panel, a light emitting diode (LED) panel, etc.

The control panel 110 may include, as shown in FIG. 6, a first setting button 261, a first setting display 271, a second setting button 262, a second setting display 272, a third setting button 263, and a third setting display 273.

The setting buttons 261, 262, and 263 may obtain a user input for selecting settings for drying. The setting displays 271, 272, and 273 may display a drying setting selected through the setting buttons 261, 262, and 263.

For example, the first setting button 261 may obtain a user input for selecting a "degree of dryness", and the first setting display 271 may display a "degree of dryness" selected by the first setting button 261. The second setting button 262 may obtain a user input for selecting an operation for "anti-wrinkle", and the second setting display 272 may display whether an operation for "anti-wrinkle", selected by the second setting button 262, is performed.

The third setting button 263 may obtain a user input for selecting "drying time", "dehumidification time", or "sterilization time", and the third setting display 273 may display "drying time", "dehumidification time", or "sterilization time" selected by the third setting button 263. For example, upon a selection of the drying course through the dial 241, the third setting button 263 may obtain a user input for selecting "drying time", and the third setting display 273 may display "drying time". Upon a selection of the dehumidification course through the dial 241, the third setting button 263 may obtain a user input for selecting "dehumidification time", and the third setting display 273 may display "dehumidification time". Upon a selection of the sterilization course through the dial 241, the third setting button 263 may obtain a user input for selecting "sterilization time", and the third setting display 273 may display "sterilization time".

For example, a user may select any one from among preset times (for example, 60 minutes, 140 minutes, 230 minutes, etc.) as "drying time", "dehumidification time", or "sterilization time" through the third setting button 263. As another example, the user may set "drying time", "dehumidification time", or "sterilization time" to a unit time (for example, 10 minutes) through the third setting button 263.

The controller 190 may be mounted, for example, on a printed circuit board provided on a rear surface of the control panel 110.

The controller 190 may be electrically connected to the drum motor 135, the heater 155, the compressor 161, the drain pump 166, the door switch 103, the door lock 104, the first temperature sensor 171, the second temperature sensor 172, the laundry weight sensor 173, the electrode sensor 180, and the control panel 110.

The controller 190 may include a processor 191 for generating control signals for controlling operations of the dryer 100, and a memory 192 for memorizing or storing programs and data for controlling operations of the dryer 100. The processor 191 and the memory 192 may be implemented as separate chips or a single chip. Also, the controller 190 may include a plurality of processors or a plurality of memories.

The processor 191 may process data and/or signals according to a program provided from the memory 192, and provide control signals to individual configurations of the dryer 100 based on a result of the processing.

The processor 191 may receive a user input from the control panel 110, and process the user input.

The processor 191 may control the control panel 110 to display a drying setting and drying operation information in response to the user input.

The processor 191 may control the drum motor 135, the heater 155, the compressor 161, the drain pump 166, and the door lock 104 based on outputs from the first temperature sensor 171, the second temperature sensor 172, the laundry weight sensor 173, and the electrode sensor 180, to perform a drying operation, a dehumidification operation, or a sterilization operation in response to the user input received through the control panel 110.

The processor 191 may include an operation circuit, a storage circuit, and a control circuit. The processor 191 may include a single chip or a plurality of chips. Also, the processor 191 may include a single core or a plurality of cores.

The memory 192 may memorize/store programs for controlling a washing operation according to the drying course, the dehumidification course, or the sterilization course, and data including a drying setting according to the drying course, a dehumidification setting according to the dehumidification course, or a sterilization setting according to the sterilization course.

The memory 192 may include a volatile memory, such as S-RAM, D-RAM, etc., and a non-volatile memory, such as ROM, EPROM, etc. The memory 192 may include a single memory device or a plurality of memory devices.

As described above, the dryer 100 may perform a drying operation for drying an object to be dried based on a user input obtained through the control panel 110, as well as performing a drying operation for drying an object to be dried based on a drying setting received through a communicator 180.

Hereinafter, operations of the dryer 100 will be described. The operations of the dryer 100 may be performed under a control of the controller 190 and/or the processor 191.

Figure 7:
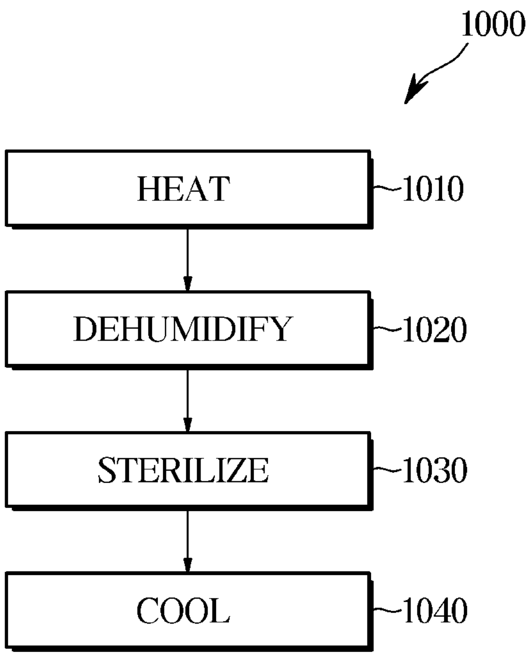
FIG. 7 schematically shows a sterilization operation of a dryer according to an embodiment.

FIG. 7 schematically shows a sterilization operation of a dryer according to an embodiment.

A sterilization operation 1000 of the dryer 100 will be described with reference to FIG. 7.

The dryer 100 may perform heating for heating air of the drum 130 and the duct 150 (1010).

The controller 190 may control the heater 155 and the fan 140 to heat air of the drum 130 and the duct 150. By an operation of the heater 155, air of the duct 150 where the heater 155 is located may be heated. Also, by an operation of the fan 140, the heated air may circulate between the drum 130 and the duct 150.

After heating, the dryer 100 may perform sterilization for removing water vapor from the air of the drum 130 and the duct 150 (1020).

The controller 190 may remove moisture and water vapor remaining in the drum 130 and the duct 150 before sterilizing the drum 130 and the duct 150.

In the drum 130 and the duct 150 being still in a hot and humid state although micro-organisms spreading in the drum 130 and the duct 150 are sterilized, micro-organisms may again spread.

The controller 190 may perform sterilization for removing moisture and water vapor from the drum 130 and the duct 150, in order to prevent micro-organisms from again spreading in the drum 130 and the duct 150.

The controller 190 may control the heater 155, the fan 140, and the heat pump 160 to remove moisture and water vapor from the drum 130 and the duct 150. For example, the controller 190 may continue to operate the heater 155 and the fan 140 operating in the heating operation. At this time, the controller 190 may change rotation velocity of the fan 140 according to an embodiment. Also, the controller 190 may start operating the compressor 161 of the heat pump 160.

By operating the compressor 161, moisture (water) remaining in the drum 130 and the duct 150 may be evaporated by the heated air, and water vapor included in the air may be condensed in the evaporator 164. As such, by evaporation and condensation, water vapor and moisture remaining in the drum 130 and the duct 150 may be collected by the evaporator 164, and the drum 130 and the duct 150 may be dehumidified.

After dehumidification, the dryer 100 may sterilize the inside of the drum 130 and the duct 150 (1030).

The controller 190 may control the heater 155, the fan 140, and the heat pump 160 to sterilize the inside of the drum 130 and the duct 150 at high temperature. The controller 190 may continue to operate the heater 155 and the fan 140 operating in the dehumidification operation. At this time, the controller 190 may change rotation velocity of the fan 140 according to an embodiment. Also, the controller 190 may stop the heat pump 160 operating in the dehumidification operation.

Sterilization may be performed on all configurations provided inside the drum 130 and the duct 150. For example, all parts through which air flows, such as the inner wall of the drum body 131, the inner wall of the front frame 105, the outlet 105*b*, the inner wall of the duct 150, the fan 140, the evaporator 164, the condenser 162, the heater 155, the rear panel 133, and the inlet 133*a*, may need to be sterilized at high temperature.

At this time, as a result of operating of the heat pump 160, the surroundings of the evaporator 164 may be cooled by evaporation of a refrigerant in the evaporator 164. Accordingly, the evaporator 164 and the surrounding air may be maintained at low temperature without being sterilized at high temperature.

To prevent this, the controller 190 may stop the heat pump 160 during the operation for high-temperature sterilization.

After sterilization, the dryer 100 may cool the inside of the drum 130 and the duct 150 (1040).

The controller 190 may cool the inside of the drum 130 and the duct 150 for a user's safety after high-temperature sterilization. The controller 190 may control the heater 155 and the fan 140 to cool the inside of the drum 130 and the duct 150. The controller 190 may continue to operate the fan 140 operating in the sterilization operation. At this time, the controller 190 may change rotation velocity of the fan 140 according to an embodiment. Also, the controller 190 may stop the heater 155 operating in the sterilization operation.

After cooling, the controller 190 may terminate the sterilization course. For example, the controller 190 may unlock the door lock 104, based on inside temperature of the drum 130, which is lower than reference temperature.

As described above, the dryer 100 may perform a sterilization course including heating, dehumidification, sterilization, and cooling on the drum 130 and the duct 150 through which air flows, during a drying operation. By the sterilization course performed on the drum 130 and the duct 150, it may be possible to suppress micro-organisms from spreading in the drum 130 and the duct 150 through which air flows, during a drying operation. Also, it may be possible to prevent or suppress an object to be dried from being contaminated by micro-organisms during a drying operation.

Figure 8:
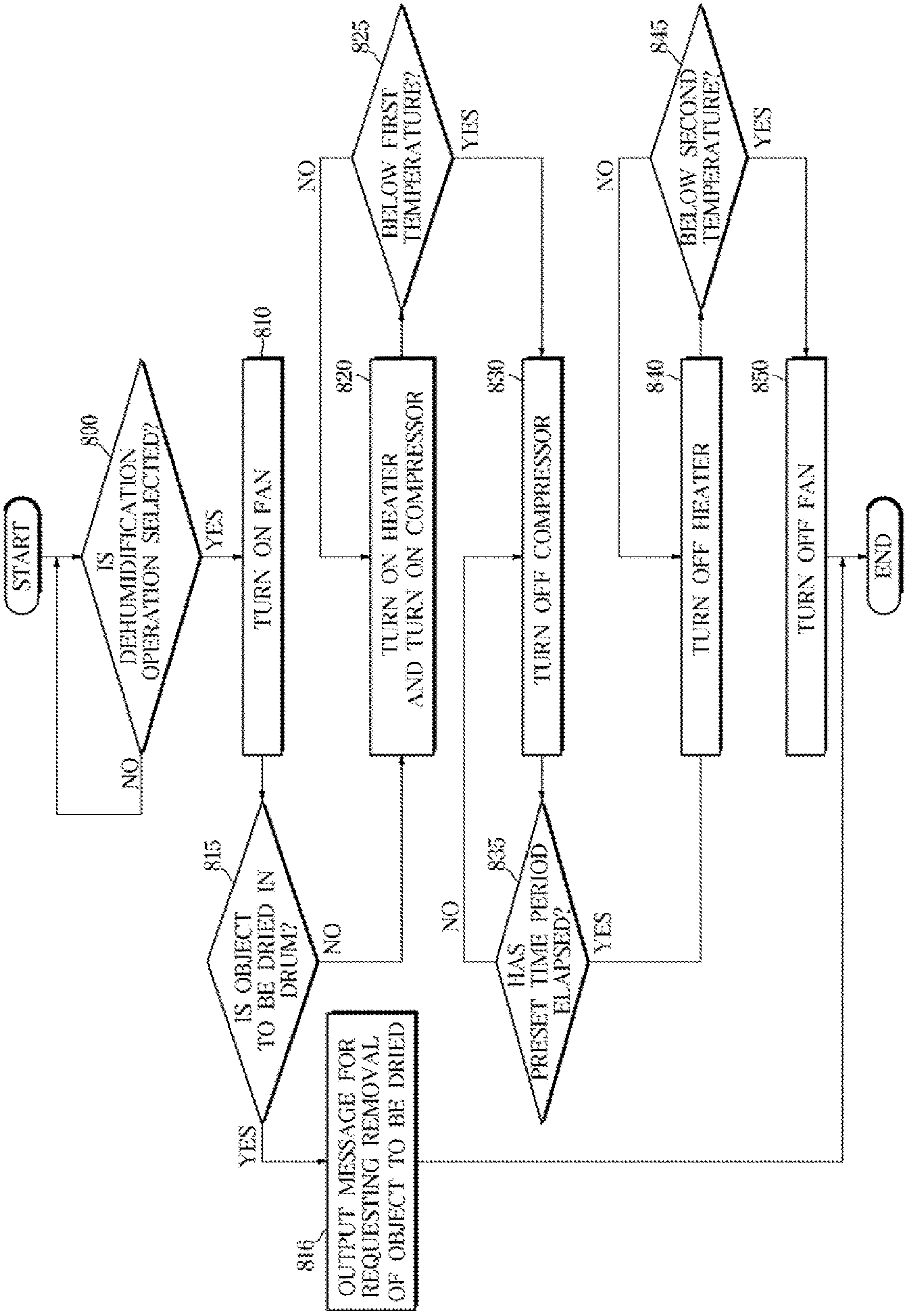
FIG. 8 is a flowchart illustrating a control method of a dryer according to an embodiment.
Figure 9:
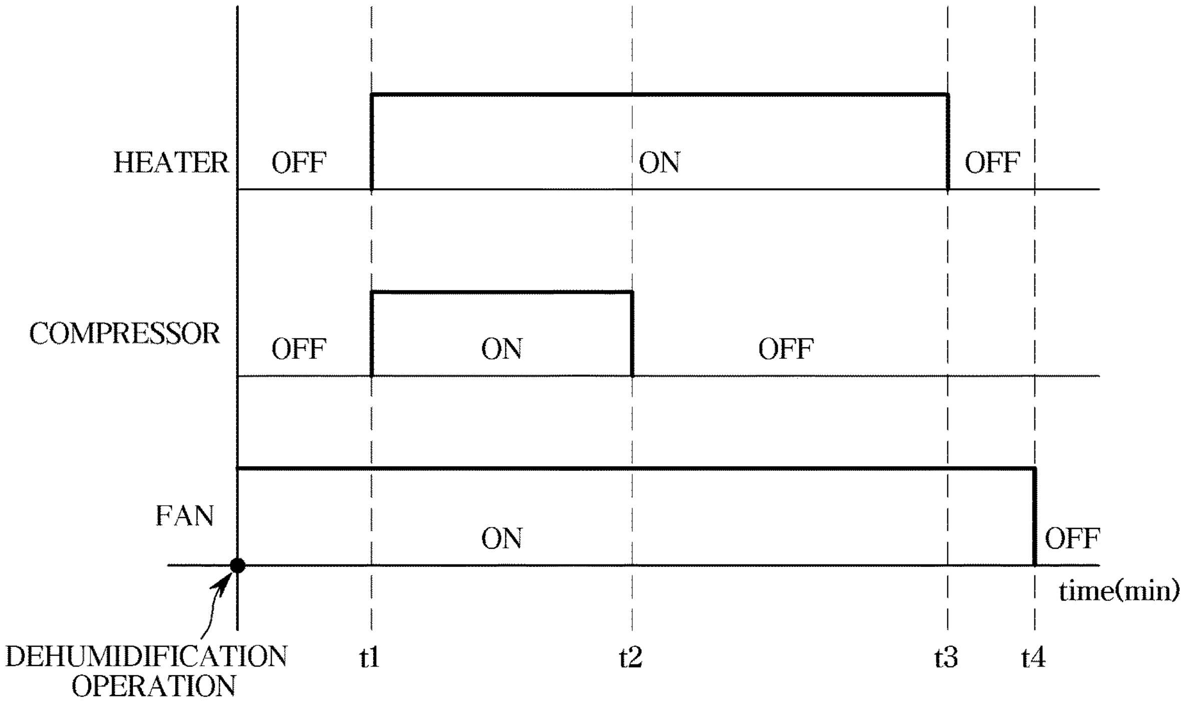
FIG. 9 shows operation times of a heater, a compressor, and a fan of a dryer according to an embodiment.

FIG. 8 is a flowchart illustrating a control method of a dryer according to an embodiment. FIG. 9 shows operation times of a heater, a compressor, and a fan of a dryer according to an embodiment.

Referring to FIG. 8, the controller 190 may determine whether an input of selecting the dehumidification course is made by a user (800).

In response to an input of selecting the dehumidification course, made on the inputter 30 (YES in 800), the controller 190 may operate the fan 140 to circulate inside air of the drum 130 (810).

More specifically, the controller 190 may control a rotation of the fan 140 by transmitting a control signal for rotating the fan 140 to the fan motor. The controller 190 may control a rotation of the drum 130 by transmitting a control signal to the drum motor 135 for rotating the drum 130.

In response to the input of selecting the dehumidification course, the controller 190 may operate the drain pump 166 before or while rotating the fan 140.

As such, by operating the drain pump 166 at an initial stage of the dehumidification course to drain water accommodated in the water bucket 165 to the outside of the dryer 100, the controller 190 may efficiently lower inside humidity of the drum 130 in the dehumidification course.

Thereafter, the controller 190 may determine whether an object to be dried is in the drum 130 (815). For example, based on a current value that is greater than or equal to a preset value, the current value sensed by the current sensor 173 that senses a current value applied to the drum motor 135, the controller 190 may determine that an object to be dried is in the drum 130. Also, based on a velocity change amount that is smaller than or equal to a preset change amount, the velocity change amount sensed by the velocity sensor 173*a* that senses a change in velocity of the drum 130, the controller 190 may determine that an object to be dried is in the drum 130.

The laundry weight sensor 173 may be a sensor not requiring a rotation of the drum 130 to sense a laundry weight, such as an image sensor for photographing the inside of the drum 130. In this case, operation 1150 of determining whether an object to be dried is in the drum 130 may be performed before operation 810 of operating the fan 140 and/or the drum motor 135.

The controller 190 may determine whether to operate the heater 155 and the compressor 161 based on whether an object to be dried is in the drum 130.

More specifically, according to an object to be dried being in the drum 130 (YES in 815), the controller 190 may stop operating the fan 140 and the drum motor 135, and control the control panel 110 to output a message for requesting removal of the object to be dried, accommodated in the drum 130 (816). In the case in which a dehumidification course is performed in a state in which an object to be dried is in the drum 130, the object to be dried may be damaged, and an effect of the dehumidification course may be not fully achieved. Therefore, by stopping operating the fan 140 and the drum motor 135 and outputting a message for requesting removal of an object to be dried, accommodated in the drum 130, the object to be dried may be prevented from being damaged, and the effect of the dehumidification course may be maximized.

At this time, the message may be output in a form of text or in all forms that can be visually recognized by a user, such as a color, a figure, etc.

The controller 190 may operate the heater 155 and the compressor 161 only according to no object to be dried being in the drum 130 (NO in 815) (820).

In this case, an operation start time of the heater 155 and/or rpm of the compressor 161 may change based on initial inside temperature of the drum 130 and/or outside temperature of the dryer 100.

For example, at sufficiently high initial inside temperature of the drum 130, the controller 190 may operate only the compressor 161 to cause inside temperature of the drum 130 to reach preset first temperature, or operate the compressor 161 at low rpm while operating the heater 155.

That is, the controller 190 may change an operation start time of the heater 155 based on temperature measured by the first temperature sensor 171. For example, in a case in which temperature measured by the first temperature sensor 171 at the time at which the controller 190 receives an input of selecting the dehumidification course is higher than or equal to preset temperature, the controller 190 may operate only the compressor 161 to raise temperature, and after temperature measured by the first temperature sensor 171 reaches the preset first temperature, the controller 190 may operate the heater 155.

In this way, at high inside temperature of the drum 130 in the initial stage of the dehumidification course, the controller 190 may change an operation start time of the heater 155 to save energy to be consumed for the operation and prevent the configurations (for example, the compressor 161) of the dryer 100 from breaking down by overheating.

However, at low outside temperature of the dryer 100 although initial inside temperature of the drum 130 is high, velocity of a temperature increase may be reduced, and accordingly, time consumed for the dehumidification course may increase.

Accordingly, although temperature measured by the first temperature sensor 171 at the time at which the controller 190 receives an input of selecting the dehumidification course is higher than or equal to the preset temperature, the controller 190 may operate the heater 155 in a case in which an increase rate of temperature measured by the first temperature sensor 171 after the operation start time of the compressor 161 is smaller than or equal to a preset value.

As such, outside temperature of the dryer 100 may be considered based on an increase rate of inside temperature of the drum 130, and by considering the outside temperature of the dryer 100, an increase of time consumed for the dehumidification course may be prevented.

As described above, the controller 190 may heat air entered the duct 150 by operating the compressor 161 and the heater 155 until inside temperature of the drum 130 reaches the preset first temperature (NO in 825).

Herein, the preset first temperature may be set to temperature that is suitable for sterilizing or dehumidifying the inside of the drum 130 and the duct 150, and the preset first temperature may be set to, for example, 70 degrees centigrade.

When inside temperature of the drum 130, that is, temperature measured by the first temperature sensor 171 increases to reach the first temperature (YES in 825), the controller 190 may stop the compressor 161 (1300), and control only the heater 155 during a preset time period to maintain inside temperature of the drum 130 at about the preset first temperature (NO in 835).

When the preset time period has elapsed after the compressor 161 stops (YES in 835), the controller 190 may stop the heater 155 (840).

By stopping the heater 155, only the fan 140 may operate, and accordingly, inside air of the duct 150 may be no longer heated. Therefore, temperature of the inside air of the duct 150 may decrease.

By stopping the heater 155, temperature measured by the first temperature sensor 171 may reach preset second temperature (YES in 845). In this case, the controller 190 may terminate the dehumidification course by stopping the fan 140 (850).

In this case, the second temperature may be set to about 50 degrees centigrade.

The above-described process of the dehumidification course will be easily understood by referring to FIG. 9.

In response to an input of selecting the dehumidification course, the controller 190 may operate the fan 140, and, when a preset time t1 has elapsed, the controller 190 may operate the heater 155 and the compressor 161. The heater 155 is shown to operate at the same time as the compressor 161, however, an operation start time of the heater 155 may change according to inside temperature of the drum 130 at a time at which the dehumidification course is selected or an increase rate of inside temperature of the drum 130 after the compressor 161 operates, as described above.

That is, the heater 155 may operate at the first time t1, between the first time t1 and a second time t2, at the second time t2, or after the second time t2.

At the time t2 at which temperature measured by the first temperature sensor 171 reaches the first temperature, the controller 190 may stop the compressor 161 and control only the heater 155 to maintain inside temperature of the drum 130.

More specifically, under an assumption that the first temperature is 70 degrees centigrade, the controller 190 may control the heater 155 in such a way as to operate the heater 155 at 69 degrees centigrade and stop the heater 155 at 71 degrees centigrade, thereby maintaining inside temperature of the drum 130.

The controller 190 may control only the heater 155 to maintain the inside temperature of the drum 130 for the preset time period, and then, at a time t3, the controller 190 may stop the heater 155 to cool the inside of the drum 130. At a time t4 at which the inside temperature of the drum 130 reaches the second temperature, the controller 190 may stop the fan 140 to terminate the entire operation.

Figure 10:
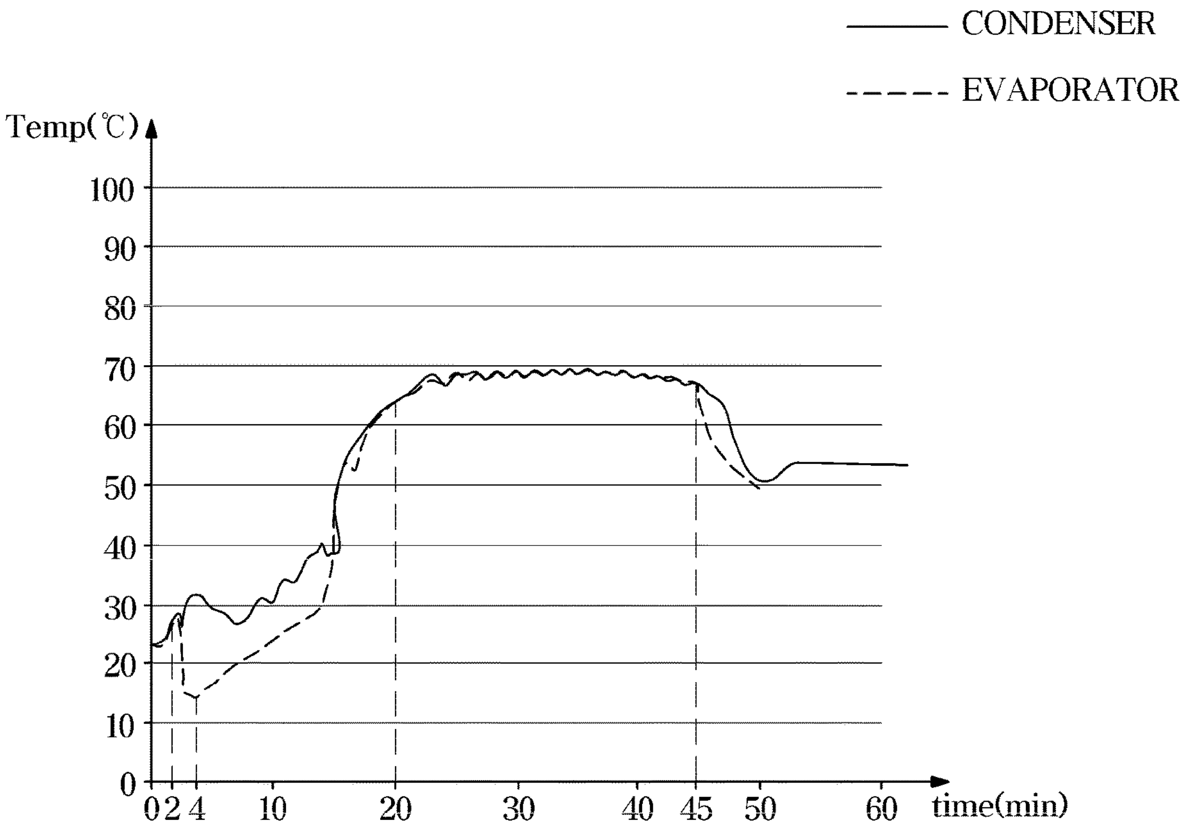
FIG. 10 shows temperature of a condenser and an evaporator over time in a dryer according to an embodiment.

FIG. 10 shows temperature of a condenser and an evaporator over time in a dryer according to an embodiment. FIG.

11 shows temperature and humidity of inside air of a drum over time in a dryer according to an embodiment.

It is seen from FIG. 10 that temperature of surrounding air of the evaporator 164 drops sharply at a time of about 2 minutes being a time at which the compressor 161 operates, and then increases gradually.

According to the sharp drop of the temperature of the surrounding air of the evaporator 164, the temperature of the surrounding air may fall below a dew point, and thus, the surrounding air may be condensed, and a part of water condensed around the evaporator 164 may remain on the evaporator 164 by surface tension.

Figure 11:
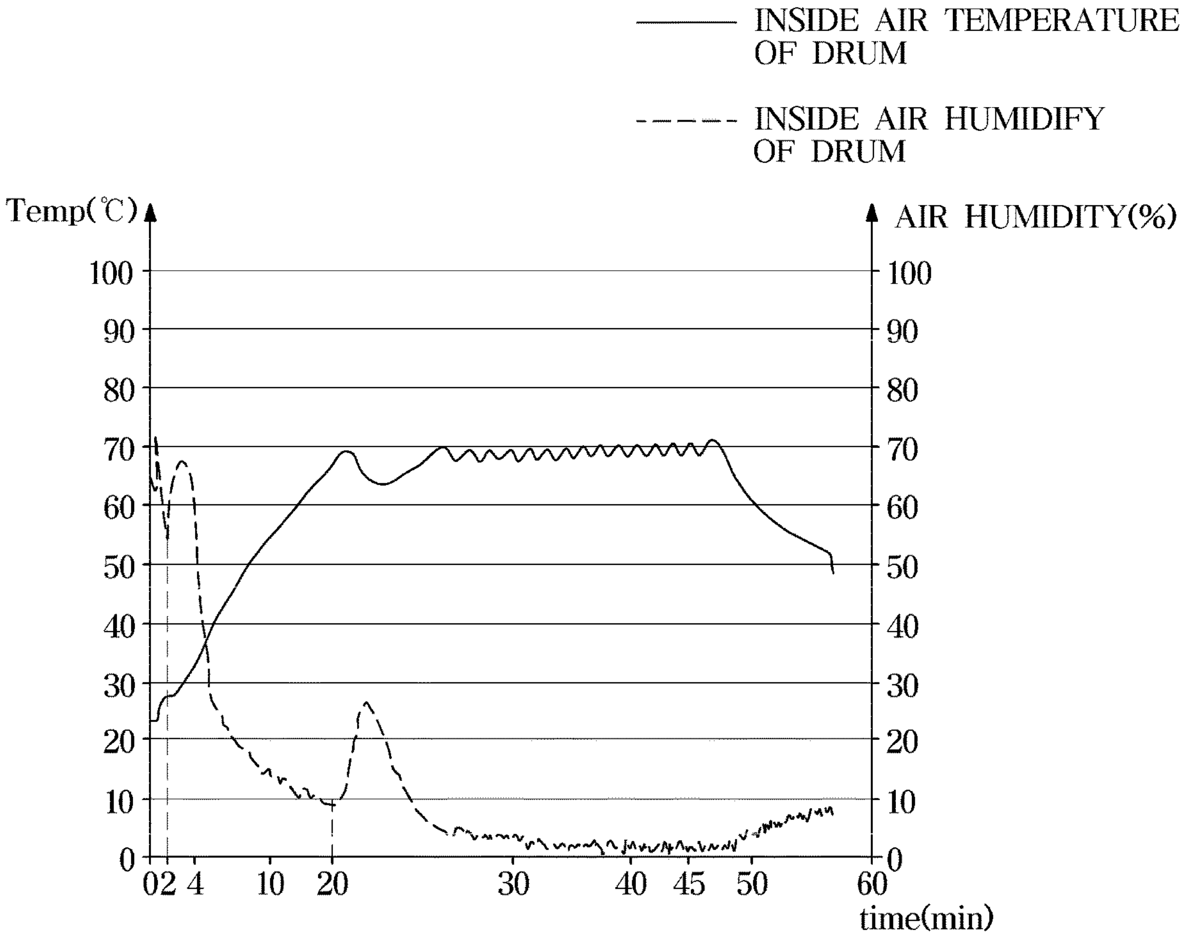
FIG. 11 shows temperature and humidity of inside air of a drum over time in a dryer according to an embodiment.

It is seen from FIG. 11 that at about 2 minutes being the time at which the compressor 161 operates, humidify of inside air of the drum 130 increases.

Likewise, at about 20 minutes being a time at which the compressor 161 stops, a temperature difference may be made between temperature of air entered the evaporator 164 and temperature of air discharged to outside of the evaporator 164, which condenses surrounding air of the evaporator 164. That is, by stopping the compressor 161, humidity of inside air of the drum 130 may again rise.

At this time, by operating only the heater 155 to maintain temperature of inside air of the drum 130 at high temperature, the humidity of the inside air of the drum 130 may be again reduced.

In a case of terminating the operation after maintaining temperature of inside air of the drum 130 at high temperature by operating the compressor 161, there may be no method for reducing humidity of inside air of the drum 130, increased by stopping the compressor 161.

Accordingly, the dryer 100 according to an embodiment may maintain both the condenser 162 and the evaporator 164 in a hot and dry state while efficiently removing moisture remaining in a lower portion of the evaporator 164, by controlling only the heater 155 for the preset time period after stopping the compressor 161 to maintain inside temperature of the drum 130.

Figure 12:
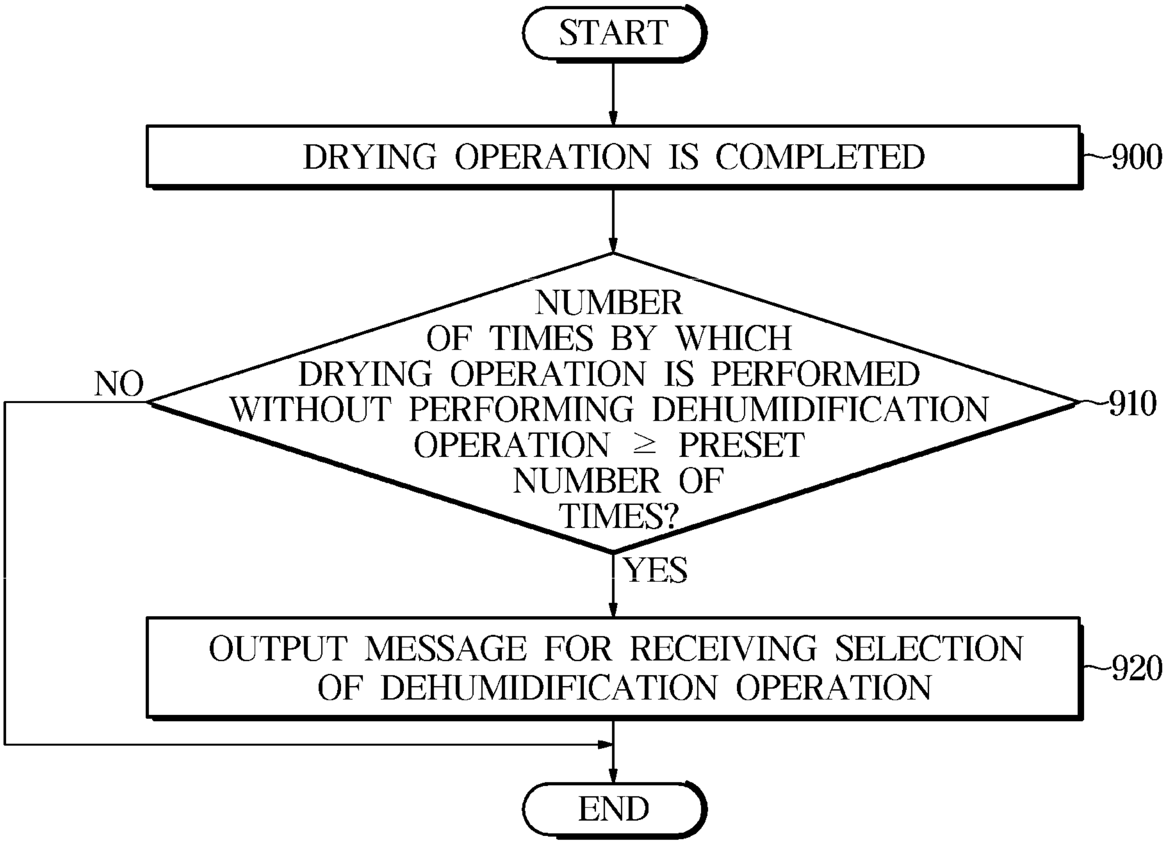
FIG. 12 is a flowchart illustrating a control method of a dryer according to another embodiment.
Figure 13:
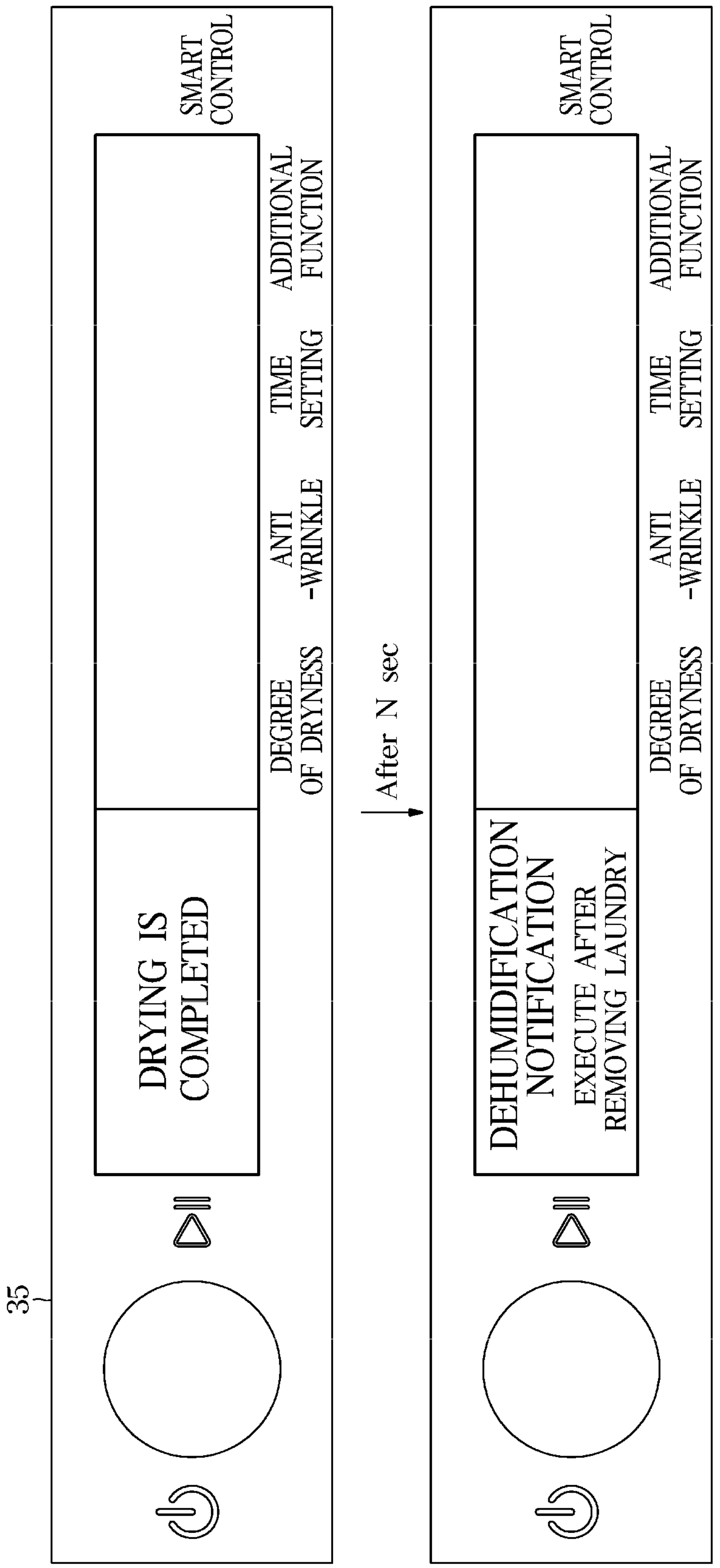
FIG. 13 shows messages output on a display of a dryer according to an embodiment.

FIG. 12 is a flowchart illustrating a control method of a dryer according to another embodiment. FIG. 13 shows messages output on a display of a dryer according to an embodiment.

Referring to FIG. 12, the controller 190 may determine whether a drying operation of the dryer 100 has been completed (900).

The drying operation may be all operations for drying an object to be dried inside the drum 130.

Upon completion of the drying operation of the dryer 100, the controller 190 may control the control panel 110 to output a message for receiving an input of selecting a dehumidification course (920).

Upon completion of a drying operation of the dryer 100, the inside of the drum 130 may be in a highest humidity state, and accordingly, condensed water may remain in the lower portion of the evaporator 164.

When a preset time period has elapsed after a drying operation is completed, a message for inducing a selection of the dehumidification course may be output to induce a user to select the dehumidification course (920).

However, frequently outputting the message may cause the user's inconvenience, and, performing the dehumidification course whenever a drying operation is completed may cause excessive power consumption and a breakdown of the compressor 161.

Accordingly, the controller 190 may determine whether a number of times by which the dryer 100 has performed a drying operation without performing a dehumidification course is more than or equal to a preset number of times (910), and the controller 190 may control, according to the number of times, by which the dryer 100 has performed the drying operation without performing the dehumidification course, being more than or equal to the preset number of times (YES in 910), the control panel 110 to output a message for receiving a selection of a dehumidification course (920).

By drying operations performed several times by the dryer 100, inside humidity of the dryer 100, particularly, humidity around the evaporator 164, which the user has difficulties in checking, may increase. An increase of inside humidity of the dryer 100 may spread micro-organisms inside the dryer 100, and accordingly, such micro-organisms may generate a bad smell inside the dryer 100.

Accordingly, by inducing, upon completion of a drying operation by the dryer 100, a user to select a dehumidification course and periodically remove moisture remaining inside the dryer 100, the spread of micro-organisms and the generation of a bad small may be prevented.

According to the disclosed embodiment, by performing a dehumidification course of operating only the heater 155 after stopping the compressor 161 to maintain high temperature, residual water formed in the inside of the dryer 100, more specifically, in the lower portion of the evaporator 164 may be effectively removed rapidly.

Also, according to the disclosed embodiment, moisture remaining around the evaporator 164, as well as inside moisture of the drum 130, may be efficiently removed.

Also, according to the disclose embodiment, by inducing a user to select a dehumidification course, the inside of the dryer 100 may be periodically dehumidified and sterilized.

Figure 14:
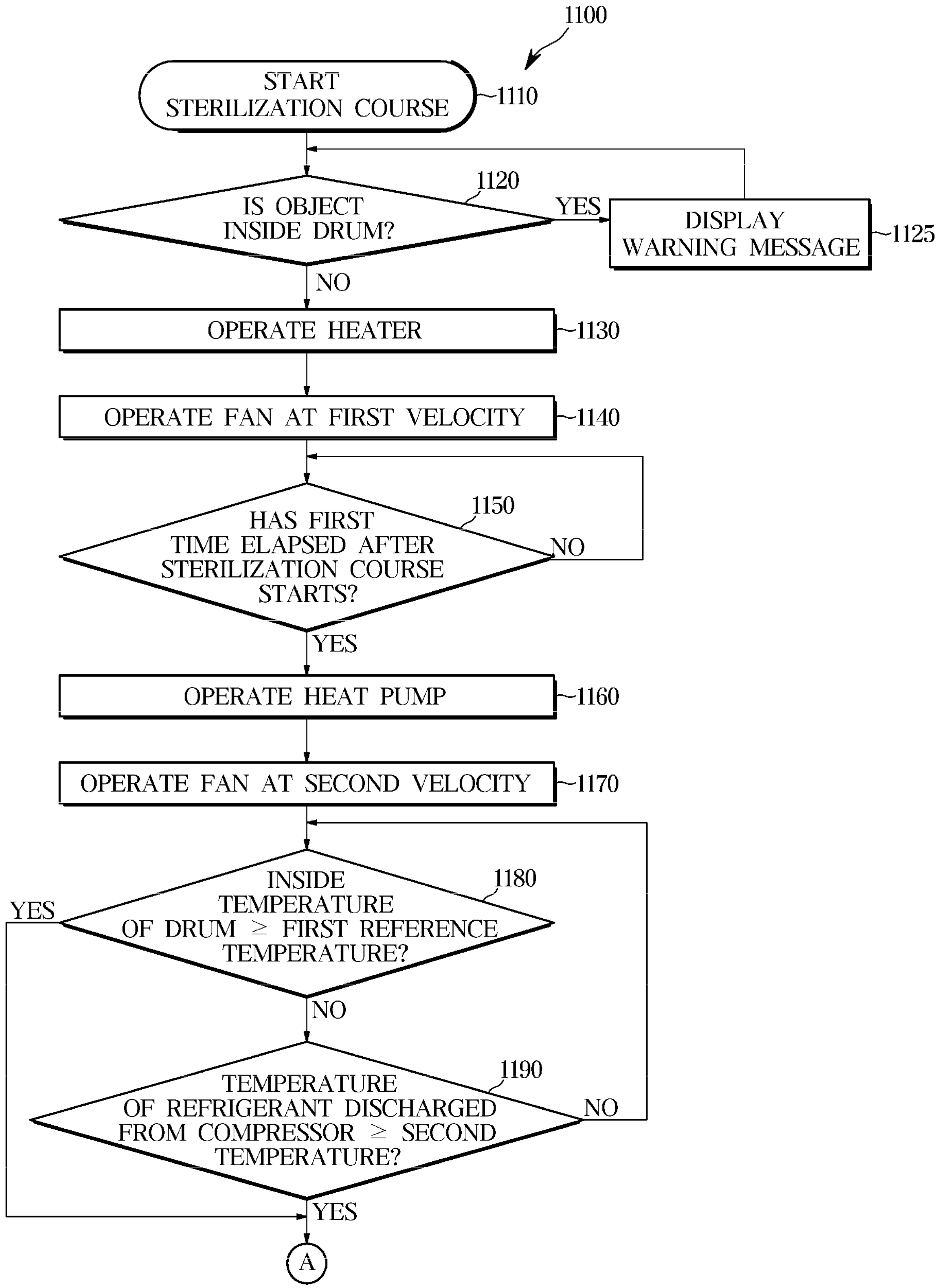
FIGS. 14 and 15 show sterilization operations of a dryer according to an embodiment.
Figure 15:
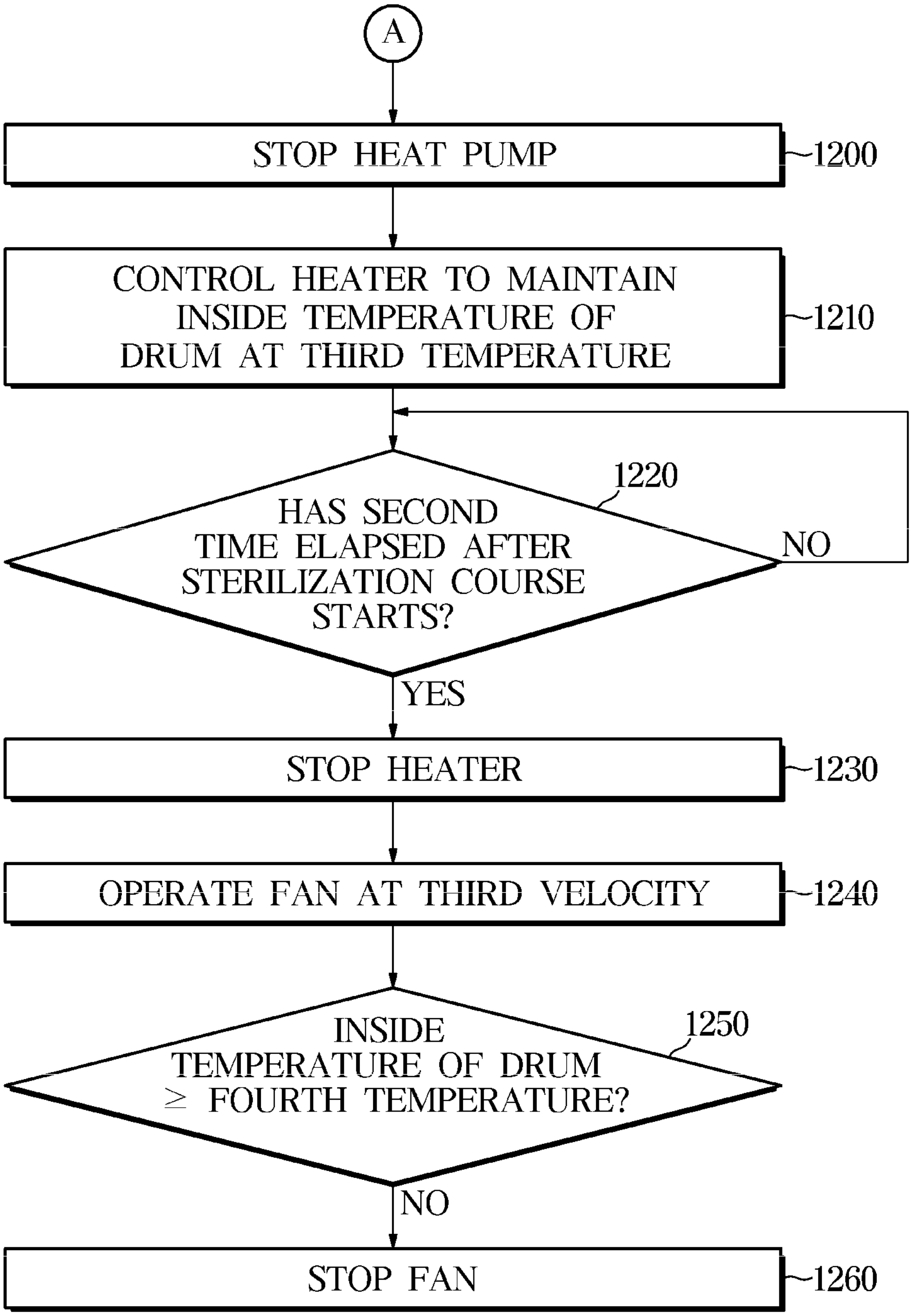
Figure 16:
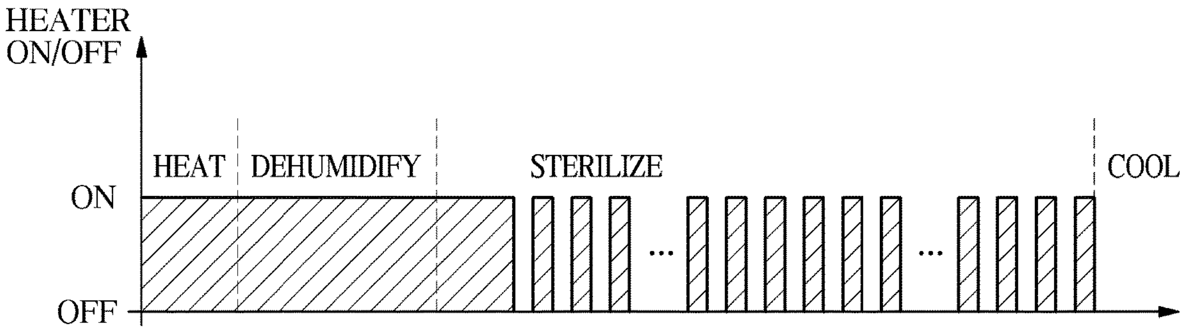
FIG. 16 shows an example of an operation of a heater during a sterilization operation according to an embodiment.
Figure 17:
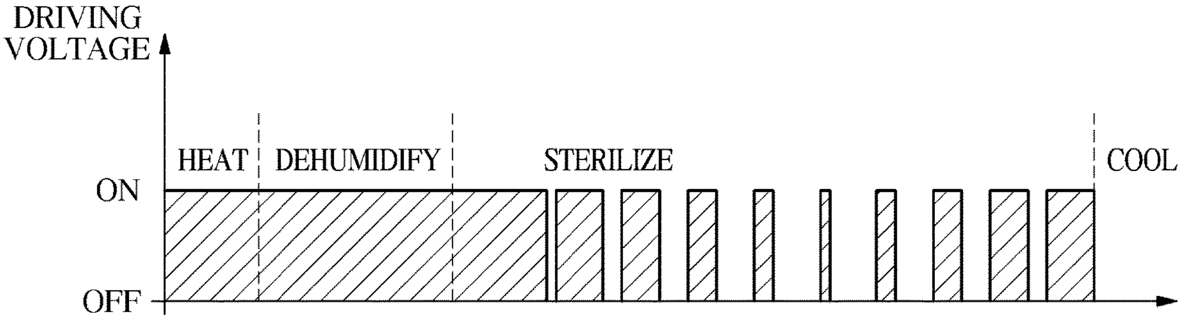
FIG. 17 shows an example of an operation of a heater during a sterilization operation according to an embodiment.
Figure 18:
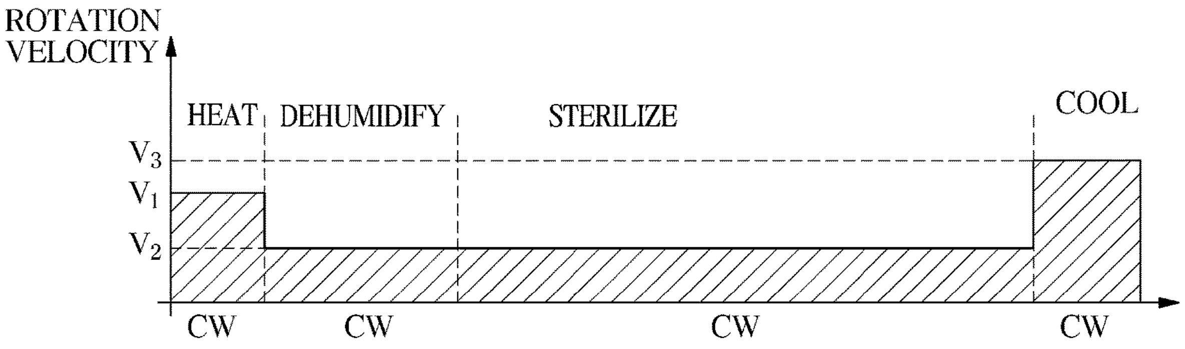
FIG. 18 shows an example of an operation of a fan during a sterilization operation according to an embodiment.
Figure 19:
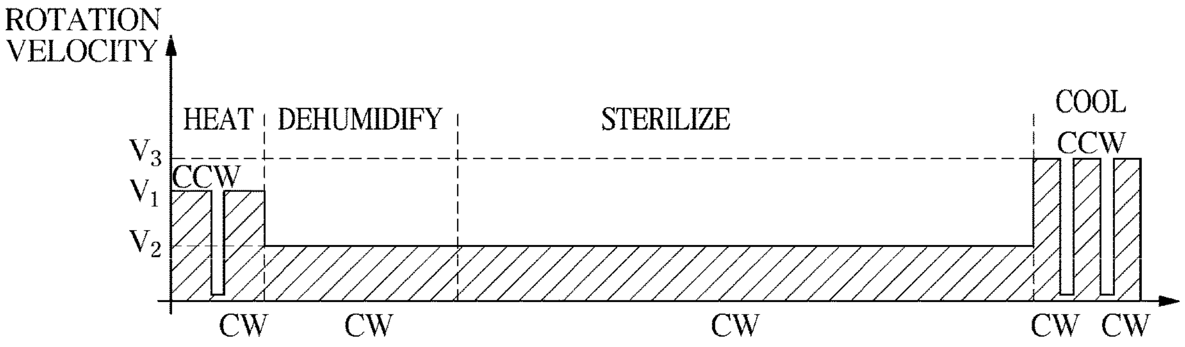
FIG. 19 shows an example of an operation of a fan during a sterilization operation according to an embodiment.
Figure 20:
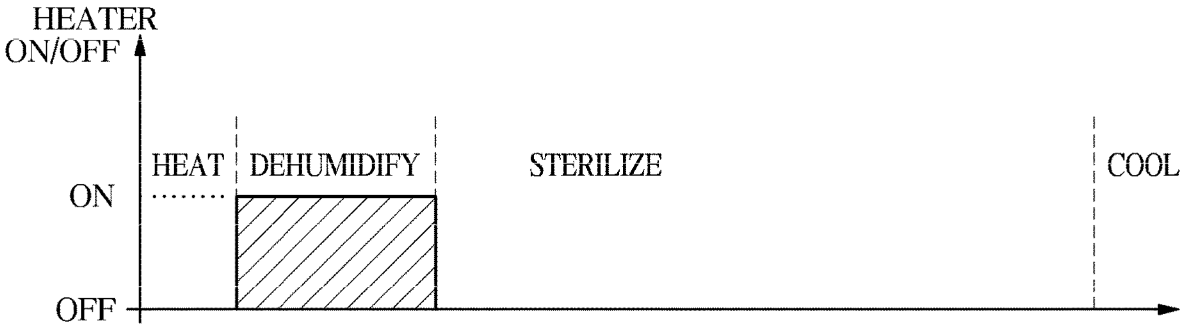
FIG. 20 shows an example of an operation of a heat pump during a sterilization operation according to an embodiment.
Figure 21:
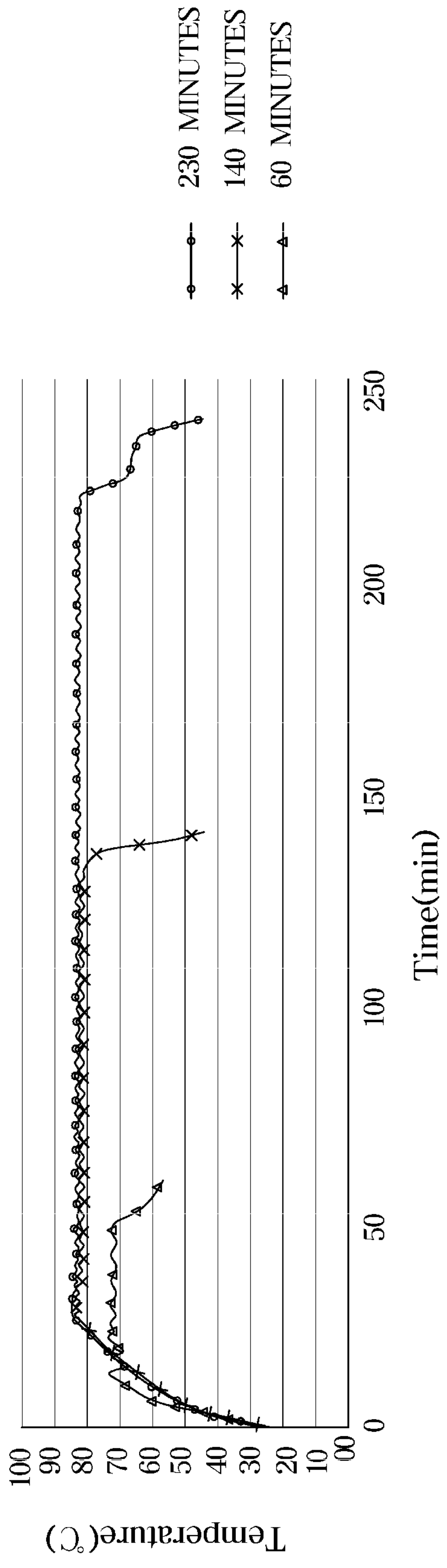
FIG. 21 shows a change in temperature of a drum during a sterilization operation according to an embodiment.

FIGS. 14 and 15 show sterilization operations of a dryer according to an embodiment. FIG. 16 shows an example of an operation of a heater during a sterilization operation according to an embodiment. FIG. 17 shows an example of an operation of a heater during a sterilization operation according to an embodiment. FIG. 18 shows an example of an operation of a fan during a sterilization operation according to an embodiment. FIG. 19 shows an example of an operation of a fan during a sterilization operation according to an embodiment. FIG. 20 shows an example of an operation of a heat pump during a sterilization operation according to an embodiment. FIG. 21 shows a change in temperature of a drum during a sterilization operation according to an embodiment.

A sterilization operation 1100 of the dryer 100 will be described with reference to FIGS. 14, 15, 16, 17, 18, 19, 20, and 21.

The dryer 100 may start a sterilization course (1110).

The control panel 110 may obtain a user input for a sterilization course from a user, and provide an electrical signal corresponding to the user input to the controller 190. For example, a sterilization course may be selected by a rotation of the dial 241, and a sterilization time may be set by the third setting button 263. Thereafter, a user input for starting the sterilization course may be obtained by the operation button 231.

The controller 190 may start an operation included in the sterilization course based on the user input through the operation button 231.

The dryer 100 may identity whether an object is inside the drum 130 (1120).

Before starting the operation included in the sterilization course, the controller 190 may identify whether an object is inside the drum 130. Inside temperature of the drum 130 in the sterilization course may be higher than inside temperature of the drum 130 in the drying course, in order to sterilize micro-organism at high temperature. Upon an object, such as clothes, etc., is inside the drum 130, the object may be deformed or damaged due to a high-temperature environment, etc.

To prevent this, the controller 190 may identify whether an object is inside the drum 130.

For example, the controller 190 may identify whether an object is inside the drum 130 by using the electrode sensor 180. The electrode sensor 180 may include the first electrode 181 and the second electrode 182.

The electrode sensor 180 may provide the controller 190 with an electrical signal corresponding to electrical resistance between the first electrode 181 and the second electrode 182 or current flowing between the first electrode 181 and the second electrode 182. The controller 190 may identify whether an object is inside the drum 130, based on an output from the electrode sensor 180. For example, the controller 190 may identity that no object is inside the drum 130, based on current of about "0" flowing between the first electrode 181 and the second electrode 182. Meanwhile, the controller 190 may identify that an object is inside the drum 130, based on current flowing between the first electrode 181 and the second electrode 182 being greater than or equal to preset reference current.

The electrode sensor 180 may provide an electrical signal corresponding to capacitance between the first electrode 181 and the second electrode 182 to the controller 190. The controller 190 may identify whether an object is inside the drum 130, based on an output from the electrode sensor 180. For example, the controller 190 may output a sensing signal to the first electrode 181, and identify whether an object is inside the drum 130 based on a response signal received from the second electrode 182.

As another example, the controller 190 may identify whether an object is inside the drum 130, based on a load of the drum motor 135. As described above, the drum motor 135 may rotate the drum 130, and driving current that is supplied to the drum motor 135 may depend on a load of the drum motor 135, that is, inertial mass of the drum 130. In other words, as objects put into the inside of the drum 130 increase, driving current that is supplied to the drum motor 135 may increase, and, as objects put into the inside of the drum 130 decrease, driving current that is supplied to the drum motor may decrease.

The controller 190 may identify whether an object is inside the drum 130, based on driving current of the drum motor 135, while rotating the drum 130. For example, the controller 190 may control the drum motor 135 to rotate the drum 130, and identify that an object is inside the drum 130, based on driving current supplied to the drum motor 135 being greater than or equal to the preset reference current.

As such, the controller 190 may identify whether an object is inside the drum 130, by various methods.

Upon an object is inside the drum 130 (YES in 1120), the dryer 100 may display a warning message for removing the object being inside the drum 130 (1125).

According to an object being inside the drum 130, the controller 190 may display a message for requesting removal of the object being inside the drum 130 on the display panel 521. For example, the controller 190 may display a message "notification of inside sterilization with hot air: execute after removing laundry" on the display panel 521.

However, instead of displaying a warning message upon an object is inside the drum 130, the controller 190 may display a message for requesting removal of an object being inside the drum 130 before starting a sterilization course. For example, while a sterilization time is set after a sterilization course is selected by a rotation of the dial 241, a message for requesting removal of an object being inside the drum 130 may be displayed on the display panel 521.

According to no object being inside the drum 130 (NO in 1120), the dryer 100 may operate the heater 155 (1130).

According to no object being inside the drum 130, the controller 190 may heat the inside of the drum 130 and the inside of the duct 150 for dehumidification and sterilization. The controller 190 may operate the heater 155 to heat the inside of the drum 130 and the inside of the duct 150, as shown in FIGS. 16 and 17.

By an operation of the heater 155 located inside the duct 150, inside temperature of the duct 150 may rise.

The dryer 100 may operate the fan 140 at first velocity V1 (1140).

According to no object being inside the drum 130, the controller 190 may operate the fan 140, while operating the heater 155. For example, both the drum 130 and the fan 140 may be connected to the drum motor 135. In this case, the controller 190 may control the drum motor 135 to rotate the drum 130 and the fan 140. As another example, the fan 140 may be connected to a fan motor provided separately from the drum motor 135. In this case, the controller 190 may control the fan motor to rotate the fan 140.

An order in which the heater 155 and the fan 140 operate is not limited to that shown in FIG. 15. For example, the controller 190 may operate the heater 155 and the fan 140 at the same time, or the controller 190 may operate the fan 140 and then operate the heater 155.

Meanwhile, the controller 190 may operate the fan 140 at preset rotation velocity in a preset rotation direction, or may change a rotation direction and/or rotation velocity of the fan 140.

For example, as shown in FIG. 18, the controller 190 may continue to operate the fan 140 at the first velocity V1 in a first direction (for example, a clockwise direction). By a rotation of the fan 140, air heated by the heater 155 may circulate between the drum 130 and the duct 150.

As another example, as shown in FIG. 19, the controller 190 may operate the fan 140 while changing the rotation direction of the fan 140. The controller 190 may rotate the fan 140 at the first velocity V1 in a second direction (for example, a counterclockwise direction), stop the fan 140 for a short time period, and then, rotate the fan 140 at the first velocity V1 in the first direction. Thereby, the flow of air may change, and heating efficiency of the insides of the drum 130 and the duct 150 may increase.

The first velocity V1 may depend on a size, capacity, etc. of the drum 130, and for example, the first velocity V1 may be between 1800 rpm and 2300 rpm.

Thereafter, the dryer 100 may identify whether a first time has elapsed after a sterilization course starts (1150).

The controller 190 may include a timer, and count a time elapsed after the sterilization course starts, by using the timer.

The controller 190 may compare the time elapsed after the sterilization course starts with the first time, and identify whether or not the time elapsed after the sterilization course starts is longer than or equal to the first time.

The time elapsed after the sterilization course starts may be equal to a time for which the heater 155 operates.

The first time may be set experimentally or empirically as a time for stabilizing a refrigerant of the heater pump 160. As described in the following operation, when the first time has elapsed after the sterilization course starts, the controller 190 may operate the heat pump 160. By operating the heat pump 160, the refrigerant may circulate inside the heat pump 160 to be repeatedly evaporated and condensed. For stable circulation of the refrigerant, the refrigerant may need to be stabilized.

For stabilization of the refrigerant, the controller 190 may not operate the heat pump 160 for the first time after the sterilization course starts. The first time may be set based on a kind and capacity of the heat pump 160, and may be set to a time between about 1 minute and about 5 minutes.

When the first time has not yet elapsed after the sterilization course starts (NO in 1150), the dryer 100 may continue to operate the heater 155 and the fan 140 to heat the drum 130 and the duct 150.

When the first time has elapsed after the sterilization course starts (YES in 1150), the dryer 100 may additionally operate the heat pump 160 (1160).

The controller 190 may dehumidify the drum 130 and the duct 150 based on the time elapsed after the sterilization course starts being longer than or equal to the first time. More specifically, as shown in FIG. 20, the controller 190 may operate the compressor 161 of the heat pump 160.

The controller 190 may operate the heat pump 160 after the refrigerant of the heat pump 160 is stabilized.

After the controller 190 stabilizes the refrigerant of the heat pump 160 for the first time, the controller 190 may operate the compressor 161 of the heat pump 160 to circulate the refrigerant. By operating the compressor 161, the refrigerant may be condensed in the condenser 161, and evaporated in the evaporator 164.

While the refrigerant is condensed in the condenser 162, the refrigerant may release heat to the condenser 162 and surrounding air of the condenser 162. Thereby, the condenser 162 and the surrounding air may be heated. The heated air may be transferred to the heater 155 by an operation of the fan 140, and again heated by the heater 155. The heated air may absorb water vapor in the drum 130 and then be transferred to the evaporator 164.

While the refrigerant is evaporated in the evaporator 164, the refrigerant may absorb heat from the evaporator 164 and surrounding air of the evaporator 164. Thereby, the evaporator 164 and the surrounding air may be cooled. Because humid air is cooled by the evaporator 164, water vapor included in the air may be condensed on a surface of the evaporator 164. Accordingly, an amount of water vapor included in the air may be reduced. In other words, by an operation of the heat pump 160, inside air of the drum 130 and the duct 150 may be dehumidified.

The dryer 100 may operate the fan 140 at second velocity V2 (1170).

When the first time has elapsed after the sterilization course starts, the controller 190 may operate the heater 155, the heat pump 160, and the fan 140 together. For example, the controller 190 may continue to operate the heater 155 and the fan 140 operating.

The controller 190 may change rotation velocity of the fan 140 operating from the first velocity V1 to the second velocity V2. For example, as shown in FIGS. 16 and 17, the second velocity V2 may be smaller than the first velocity V1. In other words, the controller 190 may reduce the rotation velocity of the fan 140. The sterilization course may be performed in a state in which no object to be dried is inside the drum 130. In other words, because no object obstructing a flow of air is inside the drum 130, air may flow rapidly inside the drum 130 and the duct 150.

Although the rotation velocity of the fan 140 is reduced, a sufficient amount of air may pass through the drum 130 and the duct 150. Accordingly, while the drum 130 and the duct 150 are dehumidified, the controller 190 may operate the fan 140 at the second velocity V2 that is smaller than the first velocity V1. Accordingly, power consumed by an operation of the drum motor 135 may be reduced.

The second velocity V2 may depend on the size, capacity, etc. of the drum 130, and the second velocity V2 may be, for example, between 1200 rpm and 1800 rpm.

An order in which operating the heat pump 160 and changing the velocity of the fan 140 are performed is not limited to that shown in FIG. 15. For example, the controller 190 may change the rotation velocity of the fan 140 while operating the heat pump 160, or the controller 190 may change the rotation velocity of the fan 140 and then operate the heat pump 160.

While the drum 130 and the duct 150 are dehumidified, the dryer 100 may identify whether or not inside temperature of the drum 130 is higher than or equal to the first temperature (1180).

The controller 190 may identify inside temperature of the drum 130 based on an output from the first temperature sensor 171. By an operation of the fan 140, inside air of the drum 130 may be discharged through the outlet 105*a*, and therefore, inside temperature of the drum 130 may be substantially similar to temperature measured by the first temperature sensor 171 installed at the outlet 105*a*.

The controller 190 may compare the inside temperature of the drum 130, based on the output from the first temperature sensor 171, with the first temperature, and identity whether or not the inside temperature of the drum 130 is higher than or equal to the first temperature.

The first temperature may be set experimentally or empirically as reference temperature for sterilizing the drum 130 and the duct 150 at high temperature. For example, the first temperature may be temperature between 55 degrees centigrade and 70 degrees centigrade.

According to the inside temperature of the drum 130 being not higher than/equal to the first temperature (NO in 1180), the dryer 100 may identify whether or not temperature of a refrigerant discharged from the compressor 161 is higher than or equal to the second temperature (1190).

The controller 190 may identify temperature of the refrigerant discharged from the compressor 161, based on an output from the second temperature sensor 172 installed at the outlet of the compressor 161.

The controller 190 may compare the temperature of the refrigerant, based on the output from the second temperature sensor 172, with the second temperature, and identify whether or not the temperature of the refrigerant discharged from the compressor 161 is higher than or equal to the second temperature. An increase of the inside temperature of the duct 150 may increase temperature of the evaporator 164 and the condenser 162 installed in the duct 150. Therefore, temperature of a refrigerant circulating through the heat pump 160 may increase, and temperature of a refrigerant discharged from the compressor 161 may also increase. Accordingly, the temperature of the refrigerant discharged from the compressor 161 may correspond to inside temperature of the duct 150.

The second temperature may be set experimentally or empirically. The second temperature may be temperature corresponding to reference temperature for sterilizing the drum 130 at high temperature. For example, the second temperature may be temperature between 80 degrees centigrade and 90 degrees centigrade.

According to the inside temperature of the drum 130 being not higher than/equal to the first temperature and the temperature of the refrigerant discharged from the compressor 161 is not higher than/equal to the second temperature (NO in 1190), the dryer 100 may repeatedly perform an operation of identifying whether or not inside temperature of the drum 130 is higher than or equal to the first temperature and identifying whether or not temperature of a refrigerant discharged from the compressor 161 is higher than or equal to the second temperature.

According to the inside temperature of the drum 130 being higher than/equal to the first temperature (YES in 1180) or that the temperature of the refrigerant discharged from the compressor 161 is higher than/equal to the second temperature (YES in 1190), the dryer 100 may stop the heat pump 160 (1200).

According to the inside temperature of the drum 130 being higher than or equal to reference temperature (first temperature) for high temperature sterilization or that the inside temperature of the duct 150 is higher than or equal to the reference temperature for high temperature sterilization (the temperature of the refrigerant is higher than or equal to the second temperature), the controller 190 may terminate the operation of dehumidifying the inside of the drum 130 and the inside of the duct 150 and start sterilization.

The controller 190 may control the heat pump 160, the heater 155, and the fan 140 to further increase inside temperature of the drum 130 and inside temperature of the duct 150 for sterilization.

The controller 190 may stop the heat pump 160 to sterilize structures being inside the drum 130 and the duct 150. In other words, the controller 190 may stop the compressor 161.

Operating the compressor 161 for a long time for high temperature sterilization may shorten the life of the compressor 161 and degrade the heat pump 160. The controller 190 may stop the heat pump 160 during high temperature sterilization to prevent the degradation of the heat pump 160.

While the compressor 161 operates, a refrigerant may circulate through the compressor 161, the condenser 162, the expander 163, and the evaporator 164. Accordingly, the refrigerant may be evaporated to cool the evaporator 164 and surrounding air of the evaporator 164. Cooling of the evaporator 164 may interfere with high temperature sterilization of the evaporator 164. Also, to heat the surroundings of the evaporator 164 cooled by an operation of the compressor 161 at high temperature for sterilization, the heater 155 may consume a great amount of power.

To sterilize the evaporator 164 at high temperature and minimize power consumption of the heater 155, the controller 190 may stop the heat pump 160 during high temperature sterilization.

However, to sterilize the inside of the drum 130 and the inside of the duct 150 at high temperature, the controller 190 may continue to operate the heater 155 and the fan 140.

While sterilizing the inside of the drum 130 and the inside of the duct 150 at high temperature, the dryer 100 may control the heater 155 to maintain inside temperature of the drum 130 at third temperature (1210).

The controller 190 may identify inside temperature (temperature of inside air) of the drum 130 based on an output from the first temperature sensor 171, and control the heater 155 based on the inside temperature (temperature of inside air) of the drum 130.

For example, as shown in FIG. 16, the controller 190 may turn on/off the heater 155 to maintain inside temperature of the drum 130 at the third temperature. The controller 190 may operate the heater 155 based on an inside temperature of the drum 130 being lower than the third temperature. Also, the controller 190 may stop the heater 155 based on an inside temperature of the drum 130 being higher than the third temperature.

As another example, as shown in FIG. 17, the controller 190 may control a supply voltage to be applied to the heater 155 such that inside temperature of the drum 130 is maintained at the third temperature. The controller 190 may perform Pulse Width Modulation (PWM) of a supply voltage based on a comparison between inside temperature of the drum 130 and the third temperature. The controller 190 may increase a duty rate of a driving voltage pulse based on an inside temperature of the drum 130 being lower than the third temperature. The controller 190 may reduce a duty rate of a driving voltage pulse based on an inside temperature of the drum 130 being higher than the third temperature. The duty rate may represent a portion of application of a driving voltage with respect to a period of a driving voltage pulse.

By controlling the heater 155, inside temperature of the drum 130 may be maintained substantially at the third temperature. Therefore, the dryer 100 may suppress excessive power consumption caused by a continuous operation of the heater 155, while maintaining temperature for high temperature sterilization. Also, internal structures of the drum 130 and the duct 150 may be prevented or suppressed from being deformed by excessively high temperature.

The third temperature may be set experimentally or empirically as temperature for sterilizing the inside of the drum 130 and the inside of the duct 150 at high temperature. For example, the third temperature may be set to temperature between 70 degrees centigrade and 85 degrees centigrade.

Also, the third temperature for high temperature sterilization may change according to a user's selection. For example, the third temperature may change depending on "sterilization time" that is selectable by a user. As shown in FIG. 21, according to a "sterilization time" setting of 60 minutes, the third temperature may be set to 70 degrees centigrade, and inside temperature of the drum 130 may be maintained at about 70 degrees centigrade. Also, according to a "sterilization time" setting of 140 minutes or 230 minutes, the third temperature may be set to 80 degrees centigrade, and inside temperature of the drum 130 may be maintained at about 80 degrees centigrade.

However, settings of the third temperature are not limited to these. An additional button for setting "sterilization temperature" for sterilization may be provided on the control panel 110, and "sterilization temperature" may be set by the additional button.

While sterilizing the inside of the drum 130 and the inside of the duct 150 at high temperature, the dryer 100 may identify whether the second time has elapsed after the sterilization course starts (1220).

The controller 190 may include a timer, and count a time elapsed after the sterilization course starts by using the timer.

The controller 190 may compare the time elapsed after the sterilization course starts with the second time, and identify whether or not the time elapsed after the sterilization course starts is longer than or equal to the second time.

The time elapsed after the sterilization course starts may be equal to a time for which the heater 155 operates.

The second time may depend on "sterilization time" set by a user through the control panel 110. For example, the second time may be set to a difference between a "sterilization time" set by a user and a time (for example, 10 minutes) for cooling. For example, according to a "sterilization time" setting of 60 minutes, the second time may be set to 50 minutes, and, according to a "sterilization time"

setting of 140 minutes, the second time may be set to 130 minutes. Also, according to a "sterilization time" setting of 230 minutes, the second time may be set to 220 minutes.

As such, by allowing various selections of sterilization temperature and a sterilization time, it may be possible to minimize energy consumption by a sterilization course and secure durability of the dryer 100, as well as executing optimized sterilization.

When the second time has not yet elapsed after the sterilization course starts (NO in 1220), the dryer 100 may continue to operate the heater 155 and the fan 140 to sterilize the drum 130 and the duct 150.

When the second time has elapsed after the sterilization course starts (YES in 1220), the dryer 100 may stop the heater 155 (1230).

Based on the time elapsed after the sterilization course starts being longer than or equal to the second time, the controller 190 may cool the drum 130 and the duct 150. More specifically, as shown in FIGS. 16 and 17, the controller 190 may stop the heater 155.

By stopping the heater 155, the drum 130 and the duct 150 may be cooled.

The dryer 100 may operate the fan 140 at third velocity V3 (1240).

When the second time has elapsed after the sterilization course starts, the controller 190 may stop the heater 155 and operate the fan 140. For example, the controller 190 may continue to operate the fan 140 operating.

The controller 190 may change rotation velocity of the fan 140 operating from the second velocity V2 to the third velocity V3. For example, as shown in FIGS. 16 and 17, the third velocity V3 may be equal to or greater than the second velocity V2. In other words, the controller 190 may maintain or increase the rotation velocity of the fan 140.

The third velocity V3 may depend on the size, capacity, etc. of the drum 130, and the third velocity V3 may be, for example, between 1800 rpm and 2300 rpm.

Meanwhile, the controller 190 may operate the fan 140 at preset rotation velocity in a preset rotation direction, or the controller 190 may change a rotation direction and/or rotation velocity of the fan 140.

For example, as shown in FIG. 18, the controller 190 may continue to operate the fan 140 at the third velocity V3 in a first direction (for example, a clockwise direction).

As another example, as shown in FIG. 19, the controller 190 may operate the fan 140 while changing the rotation direction of the fan 140. The controller 190 may rotate the fan 140 at the third velocity V3 in a second direction (for example, a counterclockwise direction), stop the fan 140 for a short time period, and then rotate the fan 140 at the third velocity V3 in the first direction. Thereby, a flow of air may change, and cooling efficiency of the insides of the drum 130 and the duct 150 may increase.

An order in which stopping the heater 155 and changing the velocity of the fan 140 are performed is not limited to that shown in FIG. 15. For example, the controller 190 may change the rotation velocity of the fan 140 while stopping the heater 155, or the controller 190 may change the rotation velocity of the fan 140 and then stop the heater 155.

While operating the fan 140, the dryer 100 may identify whether inside temperature of the drum 130 is lower than fourth temperature (1250).

The controller 190 may identify inside temperature of the drum 130 based on an output from the first temperature sensor 171. The controller 190 may compare the inside temperature of the drum 130, based on the output from the first temperature sensor 171, with the fourth temperature, and identify whether or not the inside temperature of the drum 130 is higher than or equal to the fourth temperature.

The fourth temperature may be set experimentally or empirically as reference temperature for determining whether cooling of the drum 130 and the duct 150 has been completed. For example, the fourth temperature may be temperature between 40 degrees centigrade and 50 degrees centigrade.

According to the inside temperature of the drum 130 being not lower than the fourth temperature (NO in 1250), the dryer 100 may continue to operate the fan 140 to cool the drum 130 and the duct 150.

According to the inside temperature of the drum 130 being lower than the fourth temperature (YES in 1250), the dryer 100 may stop the fan 140 (1260).

According to the inside temperature being lower than the fourth temperature, the controller 190 may stop the fan 140 and terminate the sterilization course. The controller 190 may display a message representing completion of the sterilization course on the display panel 521, and control the door lock 104 to unlock the door 102.

As described above, the dryer 100 may sterilize the duct 150 through which air for drying flows, as well as the drum 130 accommodating an object to be dried. Thereby, components on which a large amount of moisture is formed by a drying operation of the dryer 100 may be sufficiently dehumidified and sterilized.

A sterilization effect by the above-described operation will be described below.

FIG. 22 shows a sterilization effect by a sterilization operation according to an embodiment.

To verify a sterilization effect by a sterilization course of the dryer 100, *Escherichia coli* which is representative micro-organisms was used. Carriers in which micro-organisms were incubated were attached on some inner portions of the drum 130 and the duct 150, and then, a sterilization course was performed. Sterilizing rates were calculated based on a geometric mean of micro-organisms living in a carrier not sterilized and a geometric mean of micro-organisms living in a carrier sterilized by the dryer 100.

Sterilizing times were set to 140 minutes and 230 minutes.

As shown in FIG. 22, sterilizing rates obtained by the sterilization course of the dryer 100 were measured to be greater than 99% at all portions of the drum 130 and the duct 150.

More specifically, sterilization rates at the inlet 133*a* of the drum 130 were 99.96% and 99.99%, and a sterilizing rate at the filter 106 was greater than 99.99%. Sterilizing rates at the fan 140 were 99.91% and 99.97%, and a sterilizing rate at the rear duct 150 was 99.93%. A sterilizing rate at the heater 155 was 99.97%, a sterilizing rate at a front surface of the evaporator 164 was 99.99%, and a sterilizing rate at a bottom of the evaporator 164 was 99.97%. Also, a sterilizing rate at a bottom of the condenser 162 was greater than 99.99%.

As such, by the sterilization course of the dryer 100, all the inside portions of the drum 130 and the duct 150 showed sterilizing rates that are greater than 99%.

Therefore, the dryer 100 can effectively sterilize micro-organisms being in a flow path through which humid air flows for drying, and can prevent contamination and a bad smell that may be caused by micro-organisms spreading in the flow path. Also, by effective sterilization of micro-organisms, the dryer 100 may sanitarily dry an object to be dried.

So far, the sterilization course of the dryer 100, including heating, dehumidification, sterilization, and cooling, has been described, however, some of the operations may be omitted according to a sterilization time. For example, the dryer 100 may omit, based on a sterilization time that is shorter than a sterilization minimum time, sterilization and execute a sterilization course including heating, dehumidification, and cooling.

The sterilization course from which sterilization is omitted may be similar to operations shown in FIGS. 14 and 15.

For example, the dryer 100 may identify whether an object to be dried is inside the drum 130. The operation may be the same as operation 1120 described above.

According to no object to be dried is inside the drum 130, the dryer 100 may operate the heater 155 and operate the fan 155 at the first velocity V1. The operation may be the same as operation 1130 and operation 1140 described above.

The dryer 100 may identify whether a first time has elapsed after a sterilization course starts, and, when the first time has elapsed after the sterilization course starts, the dryer 100 may additionally operate the heat pump 160 for dehumidification. The dryer 100 may operate the fan 140 at the second velocity V2. Also, the dryer 100 may control the heater 155 to maintain inside temperature of the drum 130 at fifth temperature. The operation may be the same as operation 1150, operation 1160, operation 1170, and operation 1210 described above. However, the fifth temperature may be temperature for dehumidifying the insides of the drum 130 and the duct 150, and the fifth temperature may be, for example, temperature between 55 degrees centigrade and 70 degrees centigrade.

The dryer 100 may identify whether a second time has elapsed after the sterilization course starts, and, when the second time has elapsed after the sterilization course starts, the dryer 100 may stop the heat pump 160 and the heater 155.

The dryer 100 may identify whether inside temperature of the drum 130 is lower than sixth temperature, and, according to the inside temperature of the drum 130 being lower than the sixth temperature, the dryer 100 may stop the fan 140, and terminate the course. Herein, the sixth temperature may be reference temperature for determining cooling completion of the drum 130 and the duct 150, and may be, for example, temperature between 40 degrees centigrade and 50 degrees centigrade.

The dryer may include: a drum; a heat pump including an evaporator, an expander, a condenser, and a compressor; a duct accommodating the evaporator and the condenser of the heat pump, heating air entered from the drum, and discharging the heated air to the drum; a heater provided in the duct, and heating air entered the duct; a fan sucking air from inside of the drum, and discharging the sucked air to inside of the duct; a temperature sensor measuring temperature of air entered the duct from the drum; an inputter receiving an input of selecting a dehumidification course for removing inside moisture of the dryer; and a controller configured to operate the fan, according to reception of the input of selecting the dehumidification course, operate the compressor and the heater to heat air entered the duct, stop the compressor, according to a temperature measured by the temperature sensor reaching first temperature, control only the heater for a preset time period after stopping the compressor to maintain inside temperature of the drum, stop the heater when the preset time period has elapsed, and stop the fan according to a temperature measured by the temperature sensor reaching second temperature by stopping the heater.

The dryer may further include a laundry weight sensor configured to sense an amount of an object to be dried, accommodated in the drum, and the controller may determine whether an object to be dried is inside the drum, based on an output value sensed by the laundry weight sensor, and determine whether to operate the heater and the compressor, based on whether the object to be dried is inside the drum.

The controller may stop the fan and control the heater and the compressor not to operate, according to the object to be dried being inside the drum.

The dryer may further include a display, and the controller may control, according to the object to be dried being inside the drum, the display to output a message for requesting removal of the object to be dried, accommodated in the drum.

The controller may control, according to completion of a drying operation of the dryer, the display to output a message for receiving an input of selecting the dehumidification course.

The controller may control, according to a number of times, by which the dryer performs the drying operation without performing the dehumidification course, being more than or equal to a preset number of times, the display to output a message for receiving an input of selecting the dehumidification course.

The controller may change an operation start time of the heater based on temperature measured by the temperature sensor.

The controller may operate, according to a temperature measured by the temperature sensor at a time at which an input of selecting the dehumidification course is received being higher than or equal to preset temperature, the heater after temperature measured by the temperature sensor reaches the first temperature.

The controller may operate, although the temperature measured by the temperature sensor at the time at which the input of selecting the dehumidification course is received is higher than or equal to the preset temperature, the heater according to an increase rate of temperature measured by the temperature sensor after the compressor operates being smaller than or equal to a preset value.

Also, the dryer may further include: a water bucket provided below the evaporator and accommodating water condensed on the evaporator; and a drain pump discharging water accommodated in the water bucket to outside of the dryer, wherein the controller may operate the drain pump upon reception of an input of selecting the dehumidification course.

A method for controlling a dryer may include: receiving an input of selecting a dehumidification course for removing moisture from inside of the dryer; operating a fan of the dryer upon reception of the input of selecting the dehumidification course; operating a compressor and a heater of the dryer to heat air entered the duct of the dryer; stop the compressor according to a temperature of inside air of a drum of the dryer reaching first temperature; controlling only the heater for a preset time period after stopping the compressor to maintain inside temperature of the drum; stopping the heater when the preset time period has elapsed; and stopping the fan according to a temperature of the inside air of the drum reaching second temperature by stopping the heater.

The method for controlling the dryer may further include: determining whether the object to be dried is inside the drum; and determining whether to operate the heater and the compressor based on whether the object to be dried is inside the drum.

The method for controlling the dryer may further include stopping the fan and controlling the heater and the compressor not to operate according to the object to be dried being inside the drum.

The method for controlling the dryer may further include controlling, according to the object to be dried being inside the drum, the display of the dryer to output a message for requesting removal of the object to be dried, accommodated in the drum.

The method for controlling the dryer may further include controlling, upon completion of a drying operation of the dryer, the display of the dryer to output a message for receiving an input of selecting the dehumidification course.

The outputting of the message for receiving the input of selecting the dehumidification course may include controlling, according to a number of times, by which the dryer performs the drying operation without performing the dehumidification course, being more than or equal to a preset number of times, the display to output the message for receiving the input of selecting the dehumidification course.

The method for controlling the dryer may further include changing an operation start time of the heater based on inside temperature of the drum.

The changing of the operation start time of the heater based on the inside temperature of the drum may include operating the heater after inside temperature of the drum reaches the first temperature, according to an inside temperature of the drum is higher than or equal to preset temperature at a time at which the input of selecting the dehumidification course being received.

The changing of the operation start time of the heater based on the inside temperature of the drum may include operating the heater according to an increase rate of inside temperature of the drum after the operation start time of the compressor being smaller than or equal to a preset value although the inside temperature of the drum is higher than or equal to the preset temperature at the time at which the input of selecting the dehumidification course is received.

The method for controlling the dryer may further include operating a drain pump of the dryer upon reception of the input of selecting the dehumidification course.

A dryer includes: a drum; a duct connected to the drum; a compressor fluidically connected to an evaporator and a condenser provided inside the duct; a heater provided inside the duct; a fan provided inside the duct; a motor rotating the fan; and a controller configured to perform a first operation of operating the compressor, the heater, and the motor based on no object being inside the drum, and a second operation of operating the heater and the motor without operating the compressor.

Accordingly, the dryer may remove moisture and water vapor from the drum and the duct during the first operation, and sterilize micro-organisms in the drum and the duct during the second operation. Also, the dryer may sterilize the evaporator at high temperature during the second operation.

The controller may further perform a preheating operation of operating the heater and the motor without operating the compressor.

In the dryer, a refrigerant circulating through the compressor, the evaporator, and the condenser may be stabilized during the preheating operation.

The controller may control the motor to rotate the fan at first velocity during the preheating operation, and control, during the first operation and the second operation, the motor to rotate the fan at second velocity. The second velocity may be smaller than the first velocity.

By reducing rotation velocity of the fan during the first operation and the second operation, power consumption by the motor may be reduced.

The dryer may further include a first temperature sensor provided at an outlet through which air of the drum is discharged to the duct. The controller may perform the second operation based on a temperature based on an output from the first temperature sensor being higher than or equal to first temperature.

By operating the compressor to rapidly raise the inside temperature of the drum up to the first temperature, and stopping the compressor according to the inside temperature of the drum reaching the first temperature, the evaporator may be sterilized at high temperature.

The dryer may further include a second temperature sensor installed at a refrigerant outlet of the compressor. The controller may perform the second operation based on a temperature based on an output from the second temperature sensor being higher than or equal to second temperature.

By operating the compressor to rapidly raise the inside temperature of the drum up to the first temperature, and stopping the compressor according to the inside temperature of the drum reaching the first temperature, the compressor may be prevented from being overheated.

The dryer may further include a first temperature sensor provided at an outlet through which air of the drum is discharged to the duct. The controller may control the heater such that temperature based on an output from the first temperature sensor follows the second temperature.

By limiting the inside temperature of the drum to the second temperature, the drum may be prevented from being overheated.

The controller may further perform a third operation of operating the motor without operating the compressor and the heater based on an operation time of the heater being longer than or equal to a first time.

By cooling the inside of the drum, hot air circulating inside the drum may be prevented from contacting a user.

The dryer may further include a control panel configured to select a sterilization course for sterilizing the drum and the duct at high temperature, and set a sterilization time for which the sterilization course is performed. The first time may be based on the sterilization time.

A sterilization course that is controlled to various sterilization times and various sterilization temperature may be provided to a user.

The dryer may further include a front frame rotatably supporting the drum, and an electrode sensor including a pair of electrodes installed in the front frame. The controller may identify that no object is inside the drum, based on a change of an electrical resistance value or a change of capacitance between the pair of electrodes.

An object may be prevented from being damaged by high temperature sterilization.

Meanwhile, the disclosed embodiments may be implemented in the form of recording medium that stores commands executable by a computer. The commands may be stored in the form of program codes, and when executed by the processor, the commands may generate a program module to perform the operations of the disclosed embodiments. The recording medium may be implemented as computer-readable recording medium.

The computer-readable recording medium includes all kinds of recording media storing commands that can be decrypted by a computer. For example, the computer-readable recording medium may be Read Only Memory (ROM), Random Access Memory (RAM), a magnetic tape, a magnetic disk, flash memory, or an optical data storage device.

The machine-readable storage medium may be provided in the form of a non-transitory storage medium, wherein the term 'non-transitory' simply means that the storage medium is a tangible device, and does not include a signal (e.g., an electromagnetic wave), but this term does not differentiate between where data is semi-permanently stored in the storage medium and where the data is temporarily stored in the storage medium. For example, a 'non-transitory storage medium' may include a buffer in which data is temporarily stored.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloadable or uploadable) online via an application store (e.g., Play Store™) or between two user devices (e.g., smart phones) directly. When distributed online, at least part of the computer program product (e.g., a downloadable app) may be temporarily generated or at least temporarily stored in the machine-readable storage medium, such as a memory.

So far, the disclosed embodiments have been described with reference to the accompanying drawings. It will be apparent that those skilled in the art can make various modifications thereto without changing the technical spirit and essential features of the present disclosure. Thus, it should be understood that the embodiments described above are merely for illustrative purposes and not for limitation purposes in all aspects.

What is claimed is:

1. A dryer comprising:

a drum;

a duct connected to the drum;

an evaporator and a condenser provided inside the duct;

a compressor to circulate a refrigerant to the evaporator and the condenser;

a heater provided inside the duct;

a fan provided inside the duct;

a motor to rotate the fan; and a controller configured to perform a first operation of operating the compressor, the heater, and the motor based on no object being inside the drum, and a second operation of operating the heater and the motor without operating the compressor.

2. The dryer of claim 1, wherein the controller is configured to further perform a preheating operation of operating the heater and the motor without operating the compressor, control the motor to rotate the fan at a first velocity during the preheating operation, and control the motor to rotate the fan at a second velocity during the first operation and the second operation, wherein the second velocity is smaller than the first velocity.

3. The dryer of claim 1, further comprising a temperature sensor provided at an outlet through which air of the drum is discharged to the duct, wherein the controller is configured to perform the second operation based on a temperature, which is based on an output from the temperature sensor, being higher than or equal to a predetermined temperature.

4. The dryer of claim 1, further comprising a temperature sensor installed at a refrigerant outlet of the compressor, wherein the controller is configured to perform the second operation based on a temperature, which is based on an output from the temperature sensor, being higher than or equal to a predetermined temperature.

5. The dryer of claim 1, further comprising a temperature sensor provided at an outlet through which air of the drum is discharged to the duct, wherein the controller is configured to control the heater such that a temperature, which is based on an output from the temperature sensor, follows a predetermined temperature.

6. The dryer of claim 1, wherein the controller is configured to further perform a third operation of operating the motor without operating the compressor and the heater, based on an operation time of the heater being longer than or equal to a predetermined time.

7. The dryer of claim 6, further comprising a control panel configured to select a sterilization course for sterilizing the drum and the duct at high temperature, and set a sterilization time for which the sterilization course is performed, wherein the predetermined time is based on the sterilization time.

8. The dryer of claim 1, further comprising a front frame rotatably supporting the drum, and an electrode sensor including a pair of electrodes installed in the front frame, wherein the controller is configured to identify that no object is inside the drum, based on a change of an electrical resistance value or a change of capacitance between the pair of electrodes.

9. A method for controlling a dryer, the dryer including a drum, a duct connected to the drum and a fan provided inside the duct, the method comprising:

a first operation of operating a compressor connected to an evaporator and a condenser provided inside the duct, a heater provided inside the duct, and a motor to rotate the fan based on no object being inside the drum; and a second operation of operating the heater and the motor without operating the compressor.

10. The method of claim 9, further comprising a preheating operation of operating the heater and the motor without operating the compressor, wherein the preheating operation comprises operating the motor to rotate the fan at a first velocity, the first operation comprises operating the motor to rotate the fan at a second velocity, the second operation comprises operating the motor to rotate the fan at the second velocity, and the second velocity is smaller than the first velocity.

11. The method of claim 9, wherein the second operation is performed based on a temperature, which is based on an output from a temperature sensor provided at an outlet through which air of the drum is discharged to the duct, being higher than or equal to a predetermined temperature.

12. The method of claim 9, wherein the second operation is performed based on a temperature, which is based on an output from a temperature sensor installed at a refrigerant outlet of the compressor, being higher than or equal to a predetermined temperature.

13. The method of claim 9, wherein each of the first operation and the second operation comprises controlling the heater such that a temperature, which is based on an output from a temperature sensor provided at an outlet through which air of the drum is discharged to the duct, follows a predetermined temperature.

14. The method of claim 9, further comprising a third operation of operating the motor without operating the compressor and the heater based on an operation time of the heater is longer than or equal to a predetermined time.

15. The method of claim 9, further comprising identifying that no object is inside the drum, based on a change of an electrical resistance value or a change of capacitance between a pair of electrodes installed at a front frame of the dryer.

16. A dryer comprising:

a drum;

a duct connected to the drum;

a compressor connected to an evaporator and a condenser provided inside the duct;

a heater provided inside the duct;

a fan provided inside the duct;

a motor to rotate the fan; and a controller configured to operate the compressor, the heater, and the motor based on no object being inside the drum.

17. The dryer of claim 16, further comprising a temperature sensor provided at an outlet through which air of the drum is discharged to the duct, wherein the controller is configured to control the heater such that a temperature, which is based on an output from the temperature sensor, follows a predetermined temperature.

18. The dryer of claim 16, wherein the controller is configured to further perform a preheating operation of operating the heater and the motor without operating the compressor, control the motor to rotate the fan at a first velocity during the preheating operation, and control the motor to rotate the fan at a second velocity during the first operation and the second operation, wherein the second velocity is smaller than the first velocity.

19. The dryer of claim 16, wherein the controller is configured to operate the motor without operating the compressor and the heater, based on an operation time of the heater being longer than or equal to a predetermined time.

20. The dryer of claim 16, further comprising a front frame rotatably supporting the drum, and an electrode sensor including a pair of electrodes installed in the front frame, wherein the controller is configured to identify that no object is inside the drum, based on a change of an electrical resistance value or a change of capacitance between the pair of electrodes.

* * * * *